US006143869A

United States Patent [19]

Goodwin et al.

[11] Patent Number: 6,143,869

[45] Date of Patent: *Nov. 7, 2000

[54] CD30 LIGAND OLIGOMERS AND POLYPEPTIDES

[75] Inventors: Raymond G. Goodwin; Craig A. Smith, both of Seattle; Richard J. Armitage; Hans-Juergen Gruss, both of Bainbridge Island, all of Wash.

[73] Assignee: Immunex Corporation, Seattle, Wash.

[ * ] Notice: This patent is subject to a terminal disclaimer.

[21] Appl. No.: 09/079,785

[22] Filed: May 15, 1998

Related U.S. Application Data

[62] Division of application No. 08/580,014, Dec. 20, 1995, Pat. No. 5,753,203, which is a division of application No. 08/225,989, Apr. 12, 1994, Pat. No. 5,480,981, which is a continuation-in-part of application No. 07/966,775, Oct. 27, 1992, abandoned, which is a continuation-in-part of application No. 07/907,224, Jul. 1, 1992, abandoned, which is a continuation-in-part of application No. 07/899,660, Jun. 15, 1992, abandoned, which is a continuation-in-part of application No. 07/892,459, Jun. 2, 1992, abandoned, which is a continuation-in-part of application No. 07/889,717, May 26, 1992, abandoned.

[51] Int. Cl.[7] .................................................. C07K 14/435

[52] U.S. Cl. .................. 530/350; 530/387.3; 424/134.1; 424/192.1

[58] Field of Search .......................... 435/69.7; 530/350, 530/387.3; 424/134.1, 192.1

[56] References Cited

U.S. PATENT DOCUMENTS

| | | | |
|---|---|---|---|
| 5,165,923 | 11/1992 | Thorpe et al. . | |
| 5,480,981 | 1/1996 | Goodwin et al. ...................... | 536/23.5 |
| 5,753,203 | 5/1998 | Goodwin et al. ...................... | 424/1.41 |

FOREIGN PATENT DOCUMENTS

| | | |
|---|---|---|
| 0 412050 A1 | 2/1991 | European Pat. Off. . |
| WO 87/07144 | 12/1987 | WIPO . |
| WO 91/07437 | 5/1991 | WIPO . |
| WO 93/10232 | 5/1993 | WIPO . |

OTHER PUBLICATIONS

Armitage et al., "Molecular and Biological Characterization of a Murine Ligand for CD40," *Nature 357*: 80–82, 1992.

Zsebo et al., "Stem Cell Factor is Encoded at the SI Locus of the Mouse and is the Ligand for the c–kit Tyrosine Kinase Receptor," *Cell 63*: 213–224, 1990.

Schwarting et al., "Cluster report: CD30," *Leucocyte Typing IV: White Cell Differentiation Antigens*: p 419–422, Oxford University Press, 1989.

Berenbeck et al., "Detection of soluble Hodgkin–associated CD30 antigen in the sera of patients with Hodgkin's lymphoma," *Leucocyte Typing IV: White Cell Differentiation Antigens*: p 425, Oxford University Press, 1989.

Dallenbach et al., "Soluble CD30 antigen in the sera of patients with adult T–cell lymphoma/leukaemia (ATL): a marker for disease activity," *Leucocyte Typing IV: White Cell Differentiation Antigens*: p. 426–428, Oxford University Press, 1989.

Smith et al., "CD30 Antigen, a Marker for Hodgkin's Lymphoma, Is a Receptor Whose Ligand Defines an Emerging Family of Cytokines with Homology to TNF," *Cell 73*: 1349–1360, 1993.

Gruss et al., "CD30 Ligand: Molecular Cloning and Pathobiological Role in CD30–Positive Malignant Lymphomas," presented at Keystone Symposium on B and T Cell Lymphomas, Copper Mountain, CO, Apr. 17–24, 1993.

Loh et al., "Polymerase Chain Reaction with Single–Sided Specificity: Analysis of T Cell Receptor δ Chain," *Science 243*: 217–220, 1989.

Falini et al., "Response of refractory Hodgkin's disease to monoclonal anti–CD30 immunotoxin," *Lancet 339*: 1195–1196, 1992.

da Costa et al., "Immunoscintigraphy in Hodgkin's disease and anaplastic large cell lymphomas: Results in 18 patients using the iodine radiolabeled monoclonal antibody HRS–3," *Ann. Onc. 3* (*Suppl. 4*): S53–S57, 1992.

Engert et al., "Evaluation of Ricin A Chain–containing Immunotoxins Directed against the CD30 Antigen as Potential Reagents for the Treatment of Hodgkin's Disease," *Cancer Res. 50*: 84–88, 1990.

Engert et al., "Experimental therapy in Hodgkin's disease," *Ann. Onc. 3*(*Supp.4*): S97–S100, 1992.

Stein et al., "Three new lymphoid activation antigens," *Leucocyte Typing III: White Cell Differentiation Antigens*, p. 574, Oxford University Press, 1987.

Schwarting et al., "BER–H2: a new monoclonal antibody of the Ki–1 family for the detection of Hodgkin's disease in formaldehyde–fixed tissue sections," *Leucocyte Typing III: White Cell Differentiation Antigens*, pp. 574–575, Oxford University Press, 1987.

Newcom et al., "The Role of Ki–1 Antigen in the Autocrine TGFβ Growth Regulation of Reed–Sternberg Cells, Ki–1 Lymphoma Cells, and Activated Thymocytes," *Blood 80*(*10*) *Supp.1*: 305a, abstract No. 1211, Nov. 15, 1992.

Wu et al., "EBV and Tumor Progression to Ki–1 Anaplastic Large Cell Lymphoma (ALCL)," *Blood 80*(*10*) *Supp. 1*: 445a, Abstract No. 1771, Nov. 15, 1992.

Goodwin et al., "The TNF/NGF Superfamily of Receptors and Their Ligands," *J. Cell. Biochem.*, Keystone Symposia on Molecular & Cellular Biology, Suppl. 17B, abstract F020, Jan. 26–Feb. 10, 1993.

(List continued on next page.)

*Primary Examiner*—Lorraine Spector
*Attorney, Agent, or Firm*—Kathryn A. Anderson

[57] ABSTRACT

There is disclosed a polypeptide (CD30-L) and DNA sequences, vectors and transformed host cells useful in providing CD30-L polypeptides. The CD30-L polypeptide binds to the receptor known as CD30, which is expressed on a number of cell types, among which are Hodgkin's Disease tumor cells, large cell anaplastic lymphoma cells, adult T-cell leukemia (T-ALL) cells, and a number of other malignant cell types. CD30-L polypeptides find use as carriers for delivering diagnostic and cytotoxic agents to cells expressing the CD30 receptor.

8 Claims, No Drawings

OTHER PUBLICATIONS

Pallesen and Hamilton–Dutoit, "Ki–1 (CD–30) Antigen is Regularly Expressed by Tumor Cells of Embryonal Carcinoma," *Am. J. Path. 133*(*3*): 446–450, 1988.

Schwarting et al., "BER–H2: A New Anti–Ki–1 (CD30) Monoclonal Antibody Directed at a Formol–Resistant Epitope," *Blood 74*: 1678–1689, 1989.

Andreesen et al., "Human Macrophages Can Express the Hodgkin's Cell– Associated Antigen Ki–1 (CD30)," *Am. J. Path. 134*: 187–192, 1989.

Mechtersheimer and Möller, "Expression of Ki–1 Antigen (CD30) in Mesenchymal Tumors," *Cancer 66*(*8*): 1732–1737, 1990.

Gianotti et al., "Primary Cutaneous Pleomorphic T–Cell Lymphoma Expressing CD30 Antigen," *Am. J. Dermatopath. 13*(*5*): 503–508, 1991.

Burns and Dardick, "Ki–1 Positive Non–Hodgkin's Lymphomas," *Am. J. Clin. Path. 93*(*3*): 327–332, 1990.

Piris et al., "CD30 expression in non–Hodgkin's lymphoma," *Histopath. 17*: 211–218, 1990.

Miettinen, "CD30 Distribution," *Arch. Pathol. Lab. Med. 116*: 1197–1201, 1992.

Piris et al., "CD30 expression in follicular lymphoma," *Histopath. 18*: 25–29, 1991.

Maeda and Takahashi, "Characterization of skin infiltrating cells in adult T–cell leukaemia/lymphoma (ATLL): clinical, histological and immunohistochemical studies on eight cases," *Brit J. Derm. 121*: 603–612, 1989.

Eckert et al., "Follicular Lymphoid Hyperplasia of the Skin with High Content of Ki–1 Positive Lymphocytes," *Am. J. Dermatopath. 11*(*4*): 345–352, 1989.

Aruffo and Seed, "Molecular Cloning of a CD28 cDNA by a High Efficiency COS Cell Expression System," *Proc. Nat. Acad. Sci. USA 84*: 8573–8577, 1987.

Flanagan and Leder, "The kit Ligand: A Cell Surface Molecule Altered in Steel Mutant Fibroblasts," *Cell 63*: 185–194, 1990.

Josimovic–Alasevic et al., "Ki–1 (CD30) Antigen is Released by Ki–1 Positive Tumor Cells in vitro and in vivo," *Eur. J. Immunol. 19*: 157–162, 1989.

Froese et al., "Biochemical Characerization and Biosynthesis of the Ki–1 Antigen in Hodgkin–Derived and Virus–Transformed Human B and T Lymphoid Cell Lines," *J. Immunol. 139*(*6*): 2081–2087, 1987.

Shohat et al., "Inhibition of Cell Growth Mediated by Plasmids Encoding p53 Antisense," *Oncogene 1*: 277–283, 1987.

Riordan and Martin, "Oligonucleotide–based Therapeutics," *Nature 350*: 442–443, 1991.

Pfreundschuh et al., "In–vivo–Imaging von Hodgkin–Lymphomen mit monoklonalen Antikörpern," *Onkologie 12*: Supp. 1, 30–33, 1989.

Carde et al., "Immunoscintigraphy of Hodgkin's Disease: In Vivo use of Radiolabelled Monoclonal Antibodies Derived from Hodgkin Cell Lines," *Eur. J. Cancer 26*(*4*): 474–479, 1990.

Stein et al., "The Expression of the Hodgkin's Disease Associated Antigen Ki–1 in Reactive and Neoplastic Lymphoid Tissue: Evidence that Reed–Sternberg Cells and Histiocytic Malignancies Are Derived from Activated Lymphoid Cells," *Blood 66*(*4*): 848–853, 1985.

Andreesen, et al., "A Hodgkin Cell–Specific Antigen is Expressed on a Subset of Auto–and Alloactivated T (Helper) Lymphoblasts," *Blood 63*(*6*): 1299–1302, 1984.

Klein, Epstein–Barr Virus–Carrying Cells in Hodgkin's Disease, *Blood 80*(*2*): 299–301, 1992.

Poiesz, et al., "Detection and isolation of type C retrovirus particles from fresh and cultured lumphocytes of a patient with cutaneous T–cell lymphoma," *Proc. Natl. Acad. Sci. USA 77*(*12*): 7415–7419, 1980.

Schwab et al., "Production of a monoclonal antibody specific for Hodgkin and Sternberg–Reed cells of Hodgkin's disease and a subset of normal lymphoid cells," *Nature 299*: 65–67, 1982.

Stein et al., "Identification of Hodgkin and Sternberg–Reed Cells as a Unique Cell Type Derived from a Newly Detected Small–Cell Population," *Intl. J. Cancer 30*: 445–459, 1982.

Durkop et al., "Molecular Cloning and Expression of a New Member of the Nerve Growth Factor Receptor Family that is Characteristic for Hodgkin's Disease," *Cell 68*: 421–427, 1992.

Capon et al., "Designing CD4 Immunoadhesins for AIDS Therapy," *Nature 337*: 525–531, 1989.

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
(A) LENGTH: 1788 base pairs
(B) TYPE: nucleic acid
(C) STRANDEDNESS: single
(D) TOPOLOGY: linear (ii) MOLECULE TYPE: cDNA to mRNA (iii) HYPOTHETICAL: NO (iv) ANTI-SENSE: NO (vii) IMMEDIATE SOURCE:
(B) CLONE: huCD30

(ix) FEATURE:
(A) NAME/KEY: CDS
(B) LOCATION: 1..1788

(xi) SEQUENCE DESCRIPTION: SEQ ID NO:1:

```
ATG CGC GTC CTC CTC GCC GCG CTG GGA CTG CTG TTC CTG GGG GCG CTA       48
Met Arg Val Leu Leu Ala Ala Leu Gly Leu Leu Phe Leu Gly Ala Leu
  1               5                  10                  15

CGA GCC TTC CCA CAG GAT CGA CCC TTC GAG GAC ACC TGT CAT GGA AAC       96
Arg Ala Phe Pro Gln Asp Arg Pro Phe Glu Asp Thr Cys His Gly Asn
            20                  25                  30

CCC AGC CAC TAC TAT GAC AAG GCT GTC AGG AGG TGC TGT TAC CGC TGC      144
Pro Ser His Tyr Tyr Asp Lys Ala Val Arg Arg Cys Cys Tyr Arg Cys
        35                  40                  45

CCC ATG GGG CTG TTC CCG ACA CAG CAG TGC CCA CAG AGG CCT ACT GAC      192
Pro Met Gly Leu Phe Pro Thr Gln Gln Cys Pro Gln Arg Pro Thr Asp
    50                  55                  60

TGC AGG AAG CAG TGT GAG CCT GAC TAC TAC CTG GAT GAG GCC GAC CGC      240
Cys Arg Lys Gln Cys Glu Pro Asp Tyr Tyr Leu Asp Glu Ala Asp Arg
 65                  70                  75                  80

TGT ACA GCC TGC GTG ACT TGT TCT CGA GAT GAC CTC GTG GAG AAG ACG      288
Cys Thr Ala Cys Val Thr Cys Ser Arg Asp Asp Leu Val Glu Lys Thr
                 85                  90                  95

CCG TGT GCA TGG AAC TCC TCC CGT GTC TGC GAA TGT CGA CCC GGC ATG      336
Pro Cys Ala Trp Asn Ser Ser Arg Val Cys Glu Cys Arg Pro Gly Met
            100                 105                 110

TTC TGT TCC ACG TCT GCC GTC AAC TCC TGT GCC CGC TGC TTC TTC CAT      384
Phe Cys Ser Thr Ser Ala Val Asn Ser Cys Ala Arg Cys Phe Phe His
        115                 120                 125

TCT GTC TGT CCG GCA GGG ATG ATT GTC AAG TTC CCA GGC ACG GCG CAG      432
Ser Val Cys Pro Ala Gly Met Ile Val Lys Phe Pro Gly Thr Ala Gln
    130                 135                 140

AAG AAC ACG GTC TGT GAG CCG GCT TCC CCA GGG GTC AGC CCT GCC TGT      480
Lys Asn Thr Val Cys Glu Pro Ala Ser Pro Gly Val Ser Pro Ala Cys
145                 150                 155                 160

GCC AGC CCA GAG AAC TGC AAG GAA CCC TCC AGT GGC ACC ATC CCC CAG      528
Ala Ser Pro Glu Asn Cys Lys Glu Pro Ser Ser Gly Thr Ile Pro Gln
                165                 170                 175

GCC AAG CCC ACC CCG GTG TCC CCA GCA ACC TCC AGT GCC AGC ACC ATG      576
Ala Lys Pro Thr Pro Val Ser Pro Ala Thr Ser Ser Ala Ser Thr Met
            180                 185                 190
```

-continued

```
CCT GTA AGA GGG GGC ACC CGC CTC GCC CAG GAA GCT GCT TCT AAA CTG      624
Pro Val Arg Gly Gly Thr Arg Leu Ala Gln Glu Ala Ala Ser Lys Leu
        195                 200                 205

ACG AGG GCT CCC GAC TCT CCC TCC TCT GTG GGA AGG CCT AGT TCA GAT      672
Thr Arg Ala Pro Asp Ser Pro Ser Ser Val Gly Arg Pro Ser Ser Asp
    210                 215                 220

CCA GGT CTG TCC CCA ACA CAG CCA TGC CCA GAG GGG TCT GGT GAT TGC      720
Pro Gly Leu Ser Pro Thr Gln Pro Cys Pro Glu Gly Ser Gly Asp Cys
225                 230                 235                 240

AGA AAG CAG TGT GAG CCC GAC TAC TAC CTG GAC GAG GCC GGC CGC TGC      768
Arg Lys Gln Cys Glu Pro Asp Tyr Tyr Leu Asp Glu Ala Gly Arg Cys
                245                 250                 255

ACA GCC TGC GTG AGC TGT TCT CGA GAT GAC CTT GTG GAG AAG ACG CCA      816
Thr Ala Cys Val Ser Cys Ser Arg Asp Asp Leu Val Glu Lys Thr Pro
            260                 265                 270

TGT GCA TGG AAC TCC TCC CGC ACC TGC GAA TGT CGA CCT GGC ATG ATC      864
Cys Ala Trp Asn Ser Ser Arg Thr Cys Glu Cys Arg Pro Gly Met Ile
        275                 280                 285

TGT GCC ACA TCA GCC ACC AAC TCC TGT GCC CGC TGT GTC CCC TAC CCA      912
Cys Ala Thr Ser Ala Thr Asn Ser Cys Ala Arg Cys Val Pro Tyr Pro
    290                 295                 300

ATC TGT GCA GGA GAG ACG GTC ACC AAG CCC CAG GAT ATG GCT GAG AAG      960
Ile Cys Ala Gly Glu Thr Val Thr Lys Pro Gln Asp Met Ala Glu Lys
305                 310                 315                 320

GAC ACC ACC TTT GAG GCG CCA CCC CTG GGG ACC CAG CCG GAC TGC AAC     1008
Asp Thr Thr Phe Glu Ala Pro Pro Leu Gly Thr Gln Pro Asp Cys Asn
                325                 330                 335

CCC ACC CCA GAG AAT GGC GAG GCG CCT GCC AGC ACC AGC CCC ACT CAG     1056
Pro Thr Pro Glu Asn Gly Glu Ala Pro Ala Ser Thr Ser Pro Thr Gln
            340                 345                 350

AGC TTG CTG GTG GAC TCC CAG GCC AGT AAG ACG CTG CCC ATC CCA ACC     1104
Ser Leu Leu Val Asp Ser Gln Ala Ser Lys Thr Leu Pro Ile Pro Thr
        355                 360                 365

AGC GCT CCC GTC GCT CTC TCC TCC ACG GGG AAG CCC GTT CTG GAT GCA     1152
Ser Ala Pro Val Ala Leu Ser Ser Thr Gly Lys Pro Val Leu Asp Ala
    370                 375                 380

GGG CCA GTG CTC TTC TGG GTG ATC CTG GTG TTG GTT GTG GTG GTC GGC     1200
Gly Pro Val Leu Phe Trp Val Ile Leu Val Leu Val Val Val Val Gly
385                 390                 395                 400

TCC AGC GCC TTC CTC CTG TGC CAC CGG AGG GCC TGC AGG AAG CGA ATT     1248
Ser Ser Ala Phe Leu Leu Cys His Arg Arg Ala Cys Arg Lys Arg Ile
                405                 410                 415

CGG CAG AAG CTC CAC CTG TGC TAC CCG GTC CAG ACC TCC CAG CCC AAG     1296
Arg Gln Lys Leu His Leu Cys Tyr Pro Val Gln Thr Ser Gln Pro Lys
            420                 425                 430

CTA GAG CTT GTG GAT TCC AGA CCC AGG AGG AGC TCA ACG CAG CTG AGG     1344
Leu Glu Leu Val Asp Ser Arg Pro Arg Arg Ser Ser Thr Gln Leu Arg
        435                 440                 445

AGT GGT GCG TCG GTG ACA GAA CCC GTC GCG GAA GAG CGA GGG TTA ATG     1392
Ser Gly Ala Ser Val Thr Glu Pro Val Ala Glu Glu Arg Gly Leu Met
    450                 455                 460

AGC CAG CCA CTG ATG GAG ACC TGC CAC AGC GTG GGG GCA GCC TAC CTG     1440
Ser Gln Pro Leu Met Glu Thr Cys His Ser Val Gly Ala Ala Tyr Leu
465                 470                 475                 480

GAG AGC CTG CCG CTG CAG GAT GCC AGC CCG GCC GGG GGC CCC TCG TCC     1488
Glu Ser Leu Pro Leu Gln Asp Ala Ser Pro Ala Gly Gly Pro Ser Ser
                485                 490                 495

CCC AGG GAC CTT CCT GAG CCC CGG GTG TCC ACG GAG CAC ACC AAT AAC     1536
Pro Arg Asp Leu Pro Glu Pro Arg Val Ser Thr Glu His Thr Asn Asn
            500                 505                 510
```

-continued

```
AAG ATT GAG AAA ATC TAC ATC ATG AAG GCT GAC ACC GTG ATC GTG GGG     1584
Lys Ile Glu Lys Ile Tyr Ile Met Lys Ala Asp Thr Val Ile Val Gly
        515                 520                 525

ACC GTG AAG GCT GAG CTG CCG GAG GGC CGG GGC CTG GCG GGG CCA GCA     1632
Thr Val Lys Ala Glu Leu Pro Glu Gly Arg Gly Leu Ala Gly Pro Ala
    530                 535                 540

GAG CCC GAG TTG GAG GAG GAG CTG GAG GCG GAC CAT ACC CCC CAC TAC     1680
Glu Pro Glu Leu Glu Glu Glu Leu Glu Ala Asp His Thr Pro His Tyr
545                 550                 555                 560

CCC GAG CAG GAG ACA GAA CCG CCT CTG GGC AGC TGC AGC GAT GTC ATG     1728
Pro Glu Gln Glu Thr Glu Pro Pro Leu Gly Ser Cys Ser Asp Val Met
                565                 570                 575

CTC TCA GTG GAA GAG GAA GGG AAA GAA GAC CCC TTG CCC ACA GCT GCC     1776
Leu Ser Val Glu Glu Glu Gly Lys Glu Asp Pro Leu Pro Thr Ala Ala
            580                 585                 590

TCT GGA AAG TGA                                                     1788
Ser Gly Lys
        595
```

(2) INFORMATION FOR SEQ ID NO:2:

(i) SEQUENCE CHARACTERISTICS:
(A) LENGTH: 595 amino acids
(B) TYPE: amino acid
(D) TOPOLOGY: linear (ii) MOLECULE TYPE: protein (xi) SEQUENCE DESCRIPTION: SEQ ID NO:2:

```
Met Arg Val Leu Leu Ala Ala Leu Gly Leu Leu Phe Leu Gly Ala Leu
  1               5                  10                  15

Arg Ala Phe Pro Gln Asp Arg Pro Phe Glu Asp Thr Cys His Gly Asn
             20                  25                  30

Pro Ser His Tyr Tyr Asp Lys Ala Val Arg Arg Cys Cys Tyr Arg Cys
         35                  40                  45

Pro Met Gly Leu Phe Pro Thr Gln Gln Cys Pro Gln Arg Pro Thr Asp
     50                  55                  60

Cys Arg Lys Gln Cys Glu Pro Asp Tyr Tyr Leu Asp Glu Ala Asp Arg
 65                  70                  75                  80

Cys Thr Ala Cys Val Thr Cys Ser Arg Asp Asp Leu Val Glu Lys Thr
                 85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220
```

-continued

```
Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Gly Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
        595
```

(2) INFORMATION FOR SEQ ID NO:3:

(i) SEQUENCE CHARACTERISTICS:
(A) LENGTH: 699 base pairs
(B) TYPE: nucleic acid
(C) STRANDEDNESS: single -continued (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
(B) CLONE: hIgG1Fc (ix) FEATURE:
(A) NAME/KEY: CDS
(B) LOCATION: 1..696

(xi) SEQUENCE DESCRIPTION: SEQ ID NO:3:

```
GAG CCC AGA TCT TGT GAC AAA ACT CAC ACA TGC CCA CCG TGC CCA GCA       48
Glu Pro Arg Ser Cys Asp Lys Thr His Thr Cys Pro Pro Cys Pro Ala
  1               5                  10                  15

CCT GAA CTC CTG GGG GGA CCG TCA GTC TTC CTC TTC CCC CCA AAA CCC       96
Pro Glu Leu Leu Gly Gly Pro Ser Val Phe Leu Phe Pro Pro Lys Pro
             20                  25                  30

AAG GAC ACC CTC ATG ATC TCC CGG ACC CCT GAG GTC ACA TGC GTG GTG      144
Lys Asp Thr Leu Met Ile Ser Arg Thr Pro Glu Val Thr Cys Val Val
         35                  40                  45

GTG GAC GTG AGC CAC GAA GAC CCT GAG GTC AAG TTC AAC TGG TAC GTG      192
Val Asp Val Ser His Glu Asp Pro Glu Val Lys Phe Asn Trp Tyr Val
     50                  55                  60

GAC GGC GTG GAG GTG CAT AAT GCC AAG ACA AAG CCG CGG GAG GAG CAG      240
Asp Gly Val Glu Val His Asn Ala Lys Thr Lys Pro Arg Glu Glu Gln
 65                  70                  75                  80

TAC AAC AGC ACG TAC CGG GTG GTC AGC GTC CTC ACC GTC CTG CAC CAG      288
Tyr Asn Ser Thr Tyr Arg Val Val Ser Val Leu Thr Val Leu His Gln
                 85                  90                  95

GAC TGG CTG AAT GGC AAG GAC TAC AAG TGC AAG GTC TCC AAC AAA GCC      336
Asp Trp Leu Asn Gly Lys Asp Tyr Lys Cys Lys Val Ser Asn Lys Ala
            100                 105                 110

CTC CCA GCC CCC ATG CAG AAA ACC ATC TCC AAA GCC AAA GGG CAG CCC      384
Leu Pro Ala Pro Met Gln Lys Thr Ile Ser Lys Ala Lys Gly Gln Pro
        115                 120                 125

CGA GAA CCA CAG GTG TAC ACC CTG CCC CCA TCC CGG GAT GAG CTG ACC      432
Arg Glu Pro Gln Val Tyr Thr Leu Pro Pro Ser Arg Asp Glu Leu Thr
    130                 135                 140

AAG AAC CAG GTC AGC CTG ACC TGC CTG GTC AAA GGC TTC TAT CCC AGG      480
Lys Asn Gln Val Ser Leu Thr Cys Leu Val Lys Gly Phe Tyr Pro Arg
145                 150                 155                 160

CAC ATC GCC GTG GAG TGG GAG AGC AAT GGG CAG CCG GAG AAC AAC TAC      528
His Ile Ala Val Glu Trp Glu Ser Asn Gly Gln Pro Glu Asn Asn Tyr
                165                 170                 175

AAG ACC ACG CCT CCC GTG CTG GAC TCC GAC GGC TCC TTC TTC CTC TAC      576
Lys Thr Thr Pro Pro Val Leu Asp Ser Asp Gly Ser Phe Phe Leu Tyr
            180                 185                 190

AGC AAG CTC ACC GTG GAC AAG AGC AGG TGG CAG CAG GGG AAC GTC TTC      624
Ser Lys Leu Thr Val Asp Lys Ser Arg Trp Gln Gln Gly Asn Val Phe
        195                 200                 205

TCA TGC TCC GTG ATG CAT GAG GCT CTG CAC AAC CAC TAC ACG CAG AAG      672
Ser Cys Ser Val Met His Glu Ala Leu His Asn His Tyr Thr Gln Lys
    210                 215                 220

AGC CTC TCC CTG TCT CCG GGT AAA TGA                                  699
Ser Leu Ser Leu Ser Pro Gly Lys
225                 230
```

(2) INFORMATION FOR SEQ ID NO:4:

-continued (i) SEQUENCE CHARACTERISTICS:
(A) LENGTH: 232 amino acids
(B) TYPE: amino acid
(D) TOPOLOGY: linear (ii) MOLECULE TYPE: protein (xi) SEQUENCE DESCRIPTION: SEQ ID NO:4:

```
Glu Pro Arg Ser Cys Asp Lys Thr His Thr Cys Pro Pro Cys Pro Ala
  1               5                  10                  15

Pro Glu Leu Leu Gly Gly Pro Ser Val Phe Leu Phe Pro Pro Lys Pro
             20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Asp Tyr Lys Cys Lys Val Ser Asn Lys Ala
            100                 105                 110

Leu Pro Ala Pro Met Gln Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Arg
145                 150                 155                 160

His Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

(2) INFORMATION FOR SEQ ID NO:5:

(i) SEQUENCE CHARACTERISTICS:
(A) LENGTH: 720 base pairs
(B) TYPE: nucleic acid
(C) STRANDEDNESS: single
(D) TOPOLOGY: linear (ii) MOLECULE TYPE: cDNA to mRNA (iii) HYPOTHETICAL: NO (iv) ANTI-SENSE: NO (vii) IMMEDIATE SOURCE:
(B) CLONE: muCD30-L (ix) FEATURE:
(A) NAME/KEY: CDS
(B) LOCATION: 1..720

(xi) SEQUENCE DESCRIPTION: SEQ ID NO:5:

-continued

```
ATG GAG CCA GGG CTG CAA CAA GCA GGC AGC TGT GGG GCT CCT TCC CCT        48
Met Glu Pro Gly Leu Gln Gln Ala Gly Ser Cys Gly Ala Pro Ser Pro
  1               5                  10                  15

GAC CCA GCC ATG CAG GTG CAG CCC GGC TCG GTA GCC AGC CCC TGG AGA        96
Asp Pro Ala Met Gln Val Gln Pro Gly Ser Val Ala Ser Pro Trp Arg
             20                  25                  30

AGC ACG AGG CCC TGG AGA AGC ACA AGT CGC AGC TAC TTC TAC CTC AGC       144
Ser Thr Arg Pro Trp Arg Ser Thr Ser Arg Ser Tyr Phe Tyr Leu Ser
         35                  40                  45

ACC ACC GCA CTG GTG TGC CTT GTT GTG GCA GTG GCG ATC ATT CTG GTA       192
Thr Thr Ala Leu Val Cys Leu Val Val Ala Val Ala Ile Ile Leu Val
     50                  55                  60

CTG GTA GTC CAG AAA AAG GAC TCC ACT CCA AAT ACA ACT GAG AAG GCC       240
Leu Val Val Gln Lys Lys Asp Ser Thr Pro Asn Thr Thr Glu Lys Ala
 65                  70                  75                  80

CCC CTT AAA GGA GGA AAT TGC TCA GAG GAT CTC TTC TGT ACC CTG AAA       288
Pro Leu Lys Gly Gly Asn Cys Ser Glu Asp Leu Phe Cys Thr Leu Lys
                 85                  90                  95

AGT ACT CCA TCC AAG AAG TCA TGG GCC TAC CTC CAA GTG TCA AAG CAT       336
Ser Thr Pro Ser Lys Lys Ser Trp Ala Tyr Leu Gln Val Ser Lys His
            100                 105                 110

CTC AAC AAT ACC AAA CTG TCA TGG AAC GAA GAT GGC ACC ATC CAC GGA       384
Leu Asn Asn Thr Lys Leu Ser Trp Asn Glu Asp Gly Thr Ile His Gly
        115                 120                 125

CTC ATA TAC CAG GAC GGG AAC CTG ATA GTC CAA TTC CCT GGC TTG TAC       432
Leu Ile Tyr Gln Asp Gly Asn Leu Ile Val Gln Phe Pro Gly Leu Tyr
    130                 135                 140

TTC ATC GTT TGC CAA CTG CAG TTC CTC GTG CAG TGC TCA AAT CAT TCT       480
Phe Ile Val Cys Gln Leu Gln Phe Leu Val Gln Cys Ser Asn His Ser
145                 150                 155                 160

GTG GAC CTG ACA TTG CAG CTC CTC ATC AAT TCC AAG ATC AAA AAG CAG       528
Val Asp Leu Thr Leu Gln Leu Leu Ile Asn Ser Lys Ile Lys Lys Gln
                165                 170                 175

ACG TTG GTA ACA GTG TGT GAG TCT GGA GTT CAG AGT AAG AAC ATC TAC       576
Thr Leu Val Thr Val Cys Glu Ser Gly Val Gln Ser Lys Asn Ile Tyr
            180                 185                 190

CAG AAT CTC TCT CAG TTT TTG CTG CAT TAC TTA CAG GTC AAC TCT ACC       624
Gln Asn Leu Ser Gln Phe Leu Leu His Tyr Leu Gln Val Asn Ser Thr
        195                 200                 205

ATA TCA GTC AGG GTG GAT AAT TTC CAG TAT GTG GAT ACA AAC ACT TTC       672
Ile Ser Val Arg Val Asp Asn Phe Gln Tyr Val Asp Thr Asn Thr Phe
    210                 215                 220

CCT CTT GAT AAT GTG CTA TCC GTC TTC TTA TAT AGT AGC TCA GAC TGA       720
Pro Leu Asp Asn Val Leu Ser Val Phe Leu Tyr Ser Ser Ser Asp
225                 230                 235                 240
```

(2) INFORMATION FOR SEQ ID NO:6:

(i) SEQUENCE CHARACTERISTICS:
(A) LENGTH: 239 amino acids
(B) TYPE: amino acid
(D) TOPOLOGY: linear (ii) MOLECULE TYPE: protein (xi) SEQUENCE DESCRIPTION: SEQ ID NO:6:

```
Met Glu Pro Gly Leu Gln Gln Ala Gly Ser Cys Gly Ala Pro Ser Pro
  1               5                  10                  15

Asp Pro Ala Met Gln Val Gln Pro Gly Ser Val Ala Ser Pro Trp Arg
             20                  25                  30

Ser Thr Arg Pro Trp Arg Ser Thr Ser Arg Ser Tyr Phe Tyr Leu Ser
```

-continued

```
        35                  40                  45

Thr Thr Ala Leu Val Cys Leu Val Val Ala Val Ala Ile Ile Leu Val
     50                  55                  60

Leu Val Val Gln Lys Lys Asp Ser Thr Pro Asn Thr Thr Glu Lys Ala
 65                  70                  75                  80

Pro Leu Lys Gly Gly Asn Cys Ser Glu Asp Leu Phe Cys Thr Leu Lys
                 85                  90                  95

Ser Thr Pro Ser Lys Lys Ser Trp Ala Tyr Leu Gln Val Ser Lys His
            100                 105                 110

Leu Asn Asn Thr Lys Leu Ser Trp Asn Glu Asp Gly Thr Ile His Gly
        115                 120                 125

Leu Ile Tyr Gln Asp Gly Asn Leu Ile Val Gln Phe Pro Gly Leu Tyr
    130                 135                 140

Phe Ile Val Cys Gln Leu Gln Phe Leu Val Gln Cys Ser Asn His Ser
145                 150                 155                 160

Val Asp Leu Thr Leu Gln Leu Leu Ile Asn Ser Lys Ile Lys Lys Gln
                165                 170                 175

Thr Leu Val Thr Val Cys Glu Ser Gly Val Gln Ser Lys Asn Ile Tyr
            180                 185                 190

Gln Asn Leu Ser Gln Phe Leu Leu His Tyr Leu Gln Val Asn Ser Thr
        195                 200                 205

Ile Ser Val Arg Val Asp Asn Phe Gln Tyr Val Asp Thr Asn Thr Phe
    210                 215                 220

Pro Leu Asp Asn Val Leu Ser Val Phe Leu Tyr Ser Ser Ser Asp
225                 230                 235
```

(2) INFORMATION FOR SEQ ID NO:7:

(i) SEQUENCE CHARACTERISTICS:
(A) LENGTH: 705 base pairs
(B) TYPE: nucleic acid
(C) STRANDEDNESS: single
(D) TOPOLOGY: linear (ii) MOLECULE TYPE: cDNA to mRNA (vii) IMMEDIATE SOURCE:
(B) CLONE: huCD30-L (ix) FEATURE:
(A) NAME/KEY: CDS
(B) LOCATION: 1..705

(xi) SEQUENCE DESCRIPTION: SEQ ID NO:7:

```
ATG GAC CCA GGG CTG CAG CAA GCA CTC AAC GGA ATG GCC CCT CCT GGA       48
Met Asp Pro Gly Leu Gln Gln Ala Leu Asn Gly Met Ala Pro Pro Gly
  1               5                  10                  15

GAC ACA GCC ATG CAT GTG CCG GCG GGC TCC GTG GCC AGC CAC CTG GGG       96
Asp Thr Ala Met His Val Pro Ala Gly Ser Val Ala Ser His Leu Gly
            20                  25                  30

ACC ACG AGC CGC AGC TAT TTC TAT TTG ACC ACA GCC ACT CTG GCT CTG      144
Thr Thr Ser Arg Ser Tyr Phe Tyr Leu Thr Thr Ala Thr Leu Ala Leu
        35                  40                  45

TGC CTT GTC TTC ACG GTG GCC ACT ATT ATG GTG TTG GTC GTT CAG AGG      192
Cys Leu Val Phe Thr Val Ala Thr Ile Met Val Leu Val Val Gln Arg
     50                  55                  60

ACG GAC TCC ATT CCC AAC TCA CCT GAC AAC GTC CCC CTC AAA GGA GGA      240
Thr Asp Ser Ile Pro Asn Ser Pro Asp Asn Val Pro Leu Lys Gly Gly
 65                  70                  75                  80

AAT TGC TCA GAA GAC CTC TTA TGT ATC CTG AAA AGA GCT CCA TTC AAG      288
```

-continued

```
Asn Cys Ser Glu Asp Leu Leu Cys Ile Leu Lys Arg Ala Pro Phe Lys
                85                  90                  95

AAG TCA TGG GCC TAC CTC CAA GTG GCA AAG CAT CTA AAC AAA ACC AAG      336
Lys Ser Trp Ala Tyr Leu Gln Val Ala Lys His Leu Asn Lys Thr Lys
            100                 105                 110

TTG TCT TGG AAC AAA GAT GGC ATT CTC CAT GGA GTC AGA TAT CAG GAT      384
Leu Ser Trp Asn Lys Asp Gly Ile Leu His Gly Val Arg Tyr Gln Asp
        115                 120                 125

GGG AAT CTG GTG ATC CAA TTC CCT GGT TTG TAC TTC ATC ATT TGC CAA      432
Gly Asn Leu Val Ile Gln Phe Pro Gly Leu Tyr Phe Ile Ile Cys Gln
    130                 135                 140

CTG CAG TTT CTT GTA CAA TGC CCA AAT AAT TCT GTC GAT CTG AAG TTG      480
Leu Gln Phe Leu Val Gln Cys Pro Asn Asn Ser Val Asp Leu Lys Leu
145                 150                 155                 160

GAG CTT CTC ATC AAC AAG CAT ATC AAA AAA CAG GCC CTG GTG ACA GTG      528
Glu Leu Leu Ile Asn Lys His Ile Lys Lys Gln Ala Leu Val Thr Val
                165                 170                 175

TGT GAG TCT GGA ATG CAA ACG AAA CAC GTA TAC CAG AAT CTC TCT CAA      576
Cys Glu Ser Gly Met Gln Thr Lys His Val Tyr Gln Asn Leu Ser Gln
            180                 185                 190

TTC TTG CTG GAT TAC CTG CAG GTC AAC ACC ACC ATA TCA GTC AAT GTG      624
Phe Leu Leu Asp Tyr Leu Gln Val Asn Thr Thr Ile Ser Val Asn Val
        195                 200                 205

GAT ACA TTC CAG TAC ATA GAT ACA AGC ACC TTT CCT CTT GAG AAT GTG      672
Asp Thr Phe Gln Tyr Ile Asp Thr Ser Thr Phe Pro Leu Glu Asn Val
    210                 215                 220

TTG TCC ATC TTC TTA TAC AGT AAT TCA GAC TGA                          705
Leu Ser Ile Phe Leu Tyr Ser Asn Ser Asp
225                 230                 235
```

(2) INFORMATION FOR SEQ ID NO:8:

(i) SEQUENCE CHARACTERISTICS:
(A) LENGTH: 234 amino acids
(B) TYPE: amino acid
(D) TOPOLOGY: linear (ii) MOLECULE TYPE: protein (xi) SEQUENCE DESCRIPTION: SEQ ID NO:8:

```
Met Asp Pro Gly Leu Gln Gln Ala Leu Asn Gly Met Ala Pro Pro Gly
  1               5                  10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
 65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
```

-continued

```
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230
```

(2) INFORMATION FOR SEQ ID NO:9:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (vii) IMMEDIATE SOURCE:
(B) CLONE: 5' PCR Primer (xi) SEQUENCE DESCRIPTION: SEQ ID NO:9:

ATAGCGGCCG CCACCATGCG CGTCCTCCTC GCCGCGCTG 39

(2) INFORMATION FOR SEQ ID NO:10:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (vii) IMMEDIATE SOURCE:
(B) CLONE: 3' PCR Primer (xi) SEQUENCE DESCRIPTION: SEQ ID NO:10:

ACAAGATCTG GGCTCCTTCC CCGTGGAGGA GAGAGCGAC 39

(2) INFORMATION FOR SEQ ID NO:11:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (vii) IMMEDIATE SOURCE:
(B) CLONE: BGL II Adaptor (xi) SEQUENCE DESCRIPTION: SEQ ID NO:11:

GATCTGGCAA CGAAGGTACC ATGG 24

(2) INFORMATION FOR SEQ ID NO:12:

(i) SEQUENCE CHARACTERISTICS:
(A) LENGTH: 20 base pairs
(B) TYPE: nucleic acid
(C) STRANDEDNESS: single
(D) TOPOLOGY: linear -continued (ii) MOLECULE TYPE: DNA (vii) IMMEDIATE SOURCE:
(B) CLONE: BGL II Adaptor (xi) SEQUENCE DESCRIPTION: SEQ ID NO:12:

```
CCATGGTACC TTCGTTGCCA                                       20
```

(2) INFORMATION FOR SEQ ID NO:13:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (vii) IMMEDIATE SOURCE:
(B) CLONE: Upstream sequence (ix) FEATURE:
(A) NAME/KEY: CDS
(B) LOCATION: 1..33

(xi) SEQUENCE DESCRIPTION: SEQ ID NO:13:

```
ATG GGC TGT GGG GCT CCT TCC CCT GAC CCA GCC                 33
Met Gly Cys Gly Ala Pro Ser Pro Asp Pro Ala
  1               5                  10
```

(2) INFORMATION FOR SEQ ID NO:14:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO:14:

```
Met Gly Cys Gly Ala Pro Ser Pro Asp Pro Ala
  1               5                  10
```

(2) INFORMATION FOR SEQ ID NO:15:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: FLAG peptide (xi) SEQUENCE DESCRIPTION: SEQ ID NO:15:

```
Asp Tyr Lys Asp Asp Asp Asp Lys
1               5
```

(2) INFORMATION FOR SEQ ID NO:16:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA -continued (vii) IMMEDIATE SOURCE:
(B) CLONE: Murine cDNA Primer (xi) SEQUENCE DESCRIPTION: SEQ ID NO:16:

```
AGATGCTTTG ACACTTG                                                    17
```

(2) INFORMATION FOR SEQ ID NO:17:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (vii) IMMEDIATE SOURCE:
(B) CLONE: Human cDNA Primer (xi) SEQUENCE DESCRIPTION: SEQ ID NO:17:

```
ATCACCAGAT TCCCATC                                                    17
```

(2) INFORMATION FOR SEQ ID NO:18:

(i) SEQUENCE CHARACTERISTICS:
(A) LENGTH: 663 base pairs
(B) TYPE: nucleic acid
(C) STRANDEDNESS: single
(D) TOPOLOGY: linear (ii) MOLECULE TYPE: cDNA to mRNA (iii) HYPOTHETICAL: NO (iv) ANTI-SENSE: NO (vii) IMMEDIATE SOURCE:
(B) CLONE: muCD30-L (ix) FEATURE:
(A) NAME/KEY: CDS
(B) LOCATION: 1..663

(xi) SEQUENCE DESCRIPTION: SEQ ID NO:18:

```
ATG CAG GTG CAG CCC GGC TCG GTA GCC AGC CCC TGG AGA AGC ACG AGG       48
Met Gln Val Gln Pro Gly Ser Val Ala Ser Pro Trp Arg Ser Thr Arg
  1               5                  10                  15

CCC TGG AGA AGC ACA AGT CGC AGC TAC TTC TAC CTC AGC ACC ACC GCA       96
Pro Trp Arg Ser Thr Ser Arg Ser Tyr Phe Tyr Leu Ser Thr Thr Ala
                 20                  25                  30

CTG GTG TGC CTT GTT GTG GCA GTG GCG ATC ATT CTG GTA CTG GTA GTC      144
Leu Val Cys Leu Val Val Ala Val Ala Ile Ile Leu Val Leu Val Val
             35                  40                  45

CAG AAA AAG GAC TCC ACT CCA AAT ACA ACT GAG AAG GCC CCC CTT AAA      192
Gln Lys Lys Asp Ser Thr Pro Asn Thr Thr Glu Lys Ala Pro Leu Lys
     50                  55                  60

GGA GGA AAT TGC TCA GAG GAT CTC TTC TGT ACC CTG AAA AGT ACT CCA      240
Gly Gly Asn Cys Ser Glu Asp Leu Phe Cys Thr Leu Lys Ser Thr Pro
 65                  70                  75                  80

TCC AAG AAG TCA TGG GCC TAC CTC CAA GTG TCA AAG CAT CTC AAC AAT      288
Ser Lys Lys Ser Trp Ala Tyr Leu Gln Val Ser Lys His Leu Asn Asn
                 85                  90                  95

ACC AAA CTG TCA TGG AAC GAA GAT GGC ACC ATC CAC GGA CTC ATA TAC      336
Thr Lys Leu Ser Trp Asn Glu Asp Gly Thr Ile His Gly Leu Ile Tyr
            100                 105                 110

CAG GAC GGG AAC CTG ATA GTC CAA TTC CCT GGC TTG TAC TTC ATC GTT      384
Gln Asp Gly Asn Leu Ile Val Gln Phe Pro Gly Leu Tyr Phe Ile Val
```

-continued

```
        115                 120                 125

TGC CAA CTG CAG TTC CTC GTG CAG TGC TCA AAT CAT TCT GTG GAC CTG      432
Cys Gln Leu Gln Phe Leu Val Gln Cys Ser Asn His Ser Val Asp Leu
    130                 135                 140

ACA TTG CAG CTC CTC ATC AAT TCC AAG ATC AAA AAG CAG ACG TTG GTA      480
Thr Leu Gln Leu Leu Ile Asn Ser Lys Ile Lys Lys Gln Thr Leu Val
145                 150                 155                 160

ACA GTG TGT GAG TCT GGA GTT CAG AGT AAG AAC ATC TAC CAG AAT CTC      528
Thr Val Cys Glu Ser Gly Val Gln Ser Lys Asn Ile Tyr Gln Asn Leu
                165                 170                 175

TCT CAG TTT TTG CTG CAT TAC TTA CAG GTC AAC TCT ACC ATA TCA GTC      576
Ser Gln Phe Leu Leu His Tyr Leu Gln Val Asn Ser Thr Ile Ser Val
            180                 185                 190

AGG GTG GAT AAT TTC CAG TAT GTG GAT ACA AAC ACT TTC CCT CTT GAT      624
Arg Val Asp Asn Phe Gln Tyr Val Asp Thr Asn Thr Phe Pro Leu Asp
        195                 200                 205

AAT GTG CTA TCC GTC TTC TTA TAT AGT AGC TCA GAC TGA                  663
Asn Val Leu Ser Val Phe Leu Tyr Ser Ser Ser Asp
    210                 215                 220
```

(2) INFORMATION FOR SEQ ID NO:19:

(i) SEQUENCE CHARACTERISTICS:
(A) LENGTH: 220 amino acids
(B) TYPE: amino acid
(D) TOPOLOGY: linear (ii) MOLECULE TYPE: protein (xi) SEQUENCE DESCRIPTION: SEQ ID NO:19:

```
Met Gln Val Gln Pro Gly Ser Val Ala Ser Pro Trp Arg Ser Thr Arg
  1               5                  10                  15

Pro Trp Arg Ser Thr Ser Arg Ser Tyr Phe Tyr Leu Ser Thr Thr Ala
             20                  25                  30

Leu Val Cys Leu Val Val Ala Val Ala Ile Ile Leu Val Leu Val Val
         35                  40                  45

Gln Lys Lys Asp Ser Thr Pro Asn Thr Thr Glu Lys Ala Pro Leu Lys
     50                  55                  60

Gly Gly Asn Cys Ser Glu Asp Leu Phe Cys Thr Leu Lys Ser Thr Pro
 65                  70                  75                  80

Ser Lys Lys Ser Trp Ala Tyr Leu Gln Val Ser Lys His Leu Asn Asn
                 85                  90                  95

Thr Lys Leu Ser Trp Asn Glu Asp Gly Thr Ile His Gly Leu Ile Tyr
            100                 105                 110

Gln Asp Gly Asn Leu Ile Val Gln Phe Pro Gly Leu Tyr Phe Ile Val
        115                 120                 125

Cys Gln Leu Gln Phe Leu Val Gln Cys Ser Asn His Ser Val Asp Leu
    130                 135                 140

Thr Leu Gln Leu Leu Ile Asn Ser Lys Ile Lys Lys Gln Thr Leu Val
145                 150                 155                 160

Thr Val Cys Glu Ser Gly Val Gln Ser Lys Asn Ile Tyr Gln Asn Leu
                165                 170                 175

Ser Gln Phe Leu Leu His Tyr Leu Gln Val Asn Ser Thr Ile Ser Val
            180                 185                 190

Arg Val Asp Asn Phe Gln Tyr Val Asp Thr Asn Thr Phe Pro Leu Asp
        195                 200                 205

Asn Val Leu Ser Val Phe Leu Tyr Ser Ser Ser Asp
    210                 215                 220
```

-continued (2) INFORMATION FOR SEQ ID NO:20:

(i) SEQUENCE CHARACTERISTICS:
(A) LENGTH: 125 amino acids
(B) TYPE: amino acid
(C) STRANDEDNESS: single
(D) TOPOLOGY: linear (ii) MOLECULE TYPE: protein fragment (iii) HYPOTHETICAL: NO (iv) ANTI-SENSE: NO (vii) IMMEDIATE SOURCE:
(B) CLONE: huCD30 fragment (PRELIM)

(xi) SEQUENCE DESCRIPTION: SEQ ID NO:20:

```
Pro Gly Asp Thr Val Xaa His Val Pro Ala Gly Ser Glu Ala Ser His
1               5                   10                  15

Leu Gly Thr Thr Ser Arg Xaa Tyr Phe Tyr Leu Thr Thr Xaa Thr Leu
            20                  25                  30

Ala Leu Cys Leu Val Phe Thr Val Ala Thr Ile Met Val Leu Val Val
        35                  40                  45

Gln Arg Thr Asp Ser Ile Pro Asn Ser Pro Asp Asn Val Pro Leu Lys
    50                  55                  60

Gly Gly Asn Cys Ser Glu Asp Leu Leu Cys Ile Leu Lys Arg Ala Pro
65                  70                  75                  80

Phe Lys Lys Ser Trp Ala Tyr Leu Gln Val Xaa Lys His Leu Asn Lys
                85                  90                  95

Thr Xaa Leu Ser Trp Asn Lys Asp Gly Ile Leu His Gly Val Arg Tyr
            100                 105                 110

Gln Asp Gly Asn Leu Val Ile Gln Phe Pro Gly Phe Val
        115                 120                 125
```

(2) INFORMATION FOR SEQ ID NO:21:

(i) SEQUENCE CHARACTERISTICS:
(A) LENGTH: 130 amino acids
(B) TYPE: amino acid
(C) STRANDEDNESS: single
(D) TOPOLOGY: linear (ii) MOLECULE TYPE: protein fragment (iii) HYPOTHETICAL: NO (iv) ANTI-SENSE: NO (vii) IMMEDIATE SOURCE:
(B) CLONE: muCD30 fragment (PRELIM)

(xi) SEQUENCE DESCRIPTION: SEQ ID NO:21:

```
Met Gln Val Gln Pro Gly Ser Val Ala Ser Pro Trp Arg Ser Thr Arg
1               5                   10                  15

Pro Trp Arg Ser Thr Ser Arg Ser Tyr Phe Tyr Leu Ser Thr Thr Ala
            20                  25                  30

Leu Val Cys Leu Val Val Xaa Val Ala Ile Ile Leu Val Leu Val Val
        35                  40                  45

Gln Lys Lys Asp Ser Thr Pro Asn Thr Thr Glu Lys Ala Pro Leu Lys
    50                  55                  60

Gly Gly Asn Cys Ser Glu Asp Leu Phe Cys Thr Leu Lys Ser Thr Pro
65                  70                  75                  80
```

-continued

```
Ser Lys Lys Ser Trp Ala Tyr Leu Gln Val Ser Lys His Leu Asn Asn
                85                  90                  95

Thr Lys Leu Ser Trp Asn Glu Asp Gly Thr Ile His Gly Leu Ile Tyr
            100                 105                 110

Gln Asp Gly Asn Leu Ile Val Gln Phe Pro Gly Leu Tyr Phe Ile Val
        115                 120                 125

Cys Gln
    130
```

(2) INFORMATION FOR SEQ ID NO:22:

(i) SEQUENCE CHARACTERISTICS:
(A) LENGTH: 648 base pairs
(B) TYPE: nucleic acid
(C) STRANDEDNESS: single
(D) TOPOLOGY: linear (ii) MOLECULE TYPE: cDNA to mRNA (vii) IMMEDIATE SOURCE:
(B) CLONE: huCD30-L (ix) FEATURE:
(A) NAME/KEY: CDS
(B) LOCATION: 1..648

(xi) SEQUENCE DESCRIPTION: SEQ ID NO:22:

```
ATG CAT GTG CCG GCG GGC TCC GTG GCC AGC CAC CTG GGG ACC ACG AGC        48
Met His Val Pro Ala Gly Ser Val Ala Ser His Leu Gly Thr Thr Ser
  1               5                  10                  15

CGC AGC TAT TTC TAT TTG ACC ACA GCC ACT CTG GCT CTG TGC CTT GTC        96
Arg Ser Tyr Phe Tyr Leu Thr Thr Ala Thr Leu Ala Leu Cys Leu Val
            20                  25                  30

TTC ACG GTG GCC ACT ATT ATG GTG TTG GTC GTT CAG AGG ACG GAC TCC       144
Phe Thr Val Ala Thr Ile Met Val Leu Val Val Gln Arg Thr Asp Ser
        35                  40                  45

ATT CCC AAC TCA CCT GAC AAC GTC CCC CTC AAA GGA GGA AAT TGC TCA       192
Ile Pro Asn Ser Pro Asp Asn Val Pro Leu Lys Gly Gly Asn Cys Ser
    50                  55                  60

GAA GAC CTC TTA TGT ATC CTG AAA AGA GCT CCA TTC AAG AAG TCA TGG       240
Glu Asp Leu Leu Cys Ile Leu Lys Arg Ala Pro Phe Lys Lys Ser Trp
 65                  70                  75                  80

GCC TAC CTC CAA GTG GCA AAG CAT CTA AAC AAA ACC AAG TTG TCT TGG       288
Ala Tyr Leu Gln Val Ala Lys His Leu Asn Lys Thr Lys Leu Ser Trp
                85                  90                  95

AAC AAA GAT GGC ATT CTC CAT GGA GTC AGA TAT CAG GAT GGG AAT CTG       336
Asn Lys Asp Gly Ile Leu His Gly Val Arg Tyr Gln Asp Gly Asn Leu
            100                 105                 110

GTG ATC CAA TTC CCT GGT TTG TAC TTC ATC ATT TGC CAA CTG CAG TTT       384
Val Ile Gln Phe Pro Gly Leu Tyr Phe Ile Ile Cys Gln Leu Gln Phe
        115                 120                 125

CTT GTA CAA TGC CCA AAT AAT TCT GTC GAT CTG AAG TTG GAG CTT CTC       432
Leu Val Gln Cys Pro Asn Asn Ser Val Asp Leu Lys Leu Glu Leu Leu
    130                 135                 140

ATC AAC AAG CAT ATC AAA AAA CAG GCC CTG GTG ACA GTG TGT GAG TCT       480
Ile Asn Lys His Ile Lys Lys Gln Ala Leu Val Thr Val Cys Glu Ser
145                 150                 155                 160

GGA ATG CAA ACG AAA CAC GTA TAC CAG AAT CTC TCT CAA TTC TTG CTG       528
Gly Met Gln Thr Lys His Val Tyr Gln Asn Leu Ser Gln Phe Leu Leu
                165                 170                 175

GAT TAC CTG CAG GTC AAC ACC ACC ATA TCA GTC AAT GTG GAT ACA TTC       576
Asp Tyr Leu Gln Val Asn Thr Thr Ile Ser Val Asn Val Asp Thr Phe
```

-continued

```
             180                 185                 190

CAG TAC ATA GAT ACA AGC ACC TTT CCT CTT GAG AAT GTG TTG TCC ATC       624
Gln Tyr Ile Asp Thr Ser Thr Phe Pro Leu Glu Asn Val Leu Ser Ile
        195                 200                 205

TTC TTA TAC AGT AAT TCA GAC TGA                                       648
Phe Leu Tyr Ser Asn Ser Asp
    210                 215


(2) INFORMATION FOR SEQ ID NO:23:

     (i) SEQUENCE CHARACTERISTICS:
          (A) LENGTH: 215 amino acids
          (B) TYPE: amino acid
          (D) TOPOLOGY: linear

    (ii) MOLECULE TYPE: protein

    (xi) SEQUENCE DESCRIPTION: SEQ ID NO:23:

Met His Val Pro Ala Gly Ser Val Ala Ser His Leu Gly Thr Thr Ser
  1               5                  10                  15

Arg Ser Tyr Phe Tyr Leu Thr Thr Ala Thr Leu Ala Leu Cys Leu Val
             20                  25                  30

Phe Thr Val Ala Thr Ile Met Val Leu Val Val Gln Arg Thr Asp Ser
        35                  40                  45

Ile Pro Asn Ser Pro Asp Asn Val Pro Leu Lys Gly Gly Asn Cys Ser
     50                  55                  60

Glu Asp Leu Leu Cys Ile Leu Lys Arg Ala Pro Phe Lys Lys Ser Trp
 65                  70                  75                  80

Ala Tyr Leu Gln Val Ala Lys His Leu Asn Lys Thr Lys Leu Ser Trp
                 85                  90                  95

Asn Lys Asp Gly Ile Leu His Gly Val Arg Tyr Gln Asp Gly Asn Leu
            100                 105                 110

Val Ile Gln Phe Pro Gly Leu Tyr Phe Ile Ile Cys Gln Leu Gln Phe
        115                 120                 125

Leu Val Gln Cys Pro Asn Asn Ser Val Asp Leu Lys Leu Glu Leu Leu
    130                 135                 140

Ile Asn Lys His Ile Lys Lys Gln Ala Leu Val Thr Val Cys Glu Ser
145                 150                 155                 160

Gly Met Gln Thr Lys His Val Tyr Gln Asn Leu Ser Gln Phe Leu Leu
                165                 170                 175

Asp Tyr Leu Gln Val Asn Thr Thr Ile Ser Val Asn Val Asp Thr Phe
            180                 185                 190

Gln Tyr Ile Asp Thr Ser Thr Phe Pro Leu Glu Asn Val Leu Ser Ile
        195                 200                 205

Phe Leu Tyr Ser Asn Ser Asp
    210                 215
```

CD30 LIGAND OLIGOMERS AND POLYPEPTIDES

CROSS-REFERENCE TO RELATED APPLICATIONS

This application is a divisional of U.S. application Ser. No. 08/580,014, filed Dec. 20, 1995, issued as U.S. Pat. No. 5,753,203, which is a divisional of U.S. application Ser. No. 08/225,989, filed Apr. 12, 1994, now U.S. Pat. No. 5,480,981, which is a continuation-in-part of U.S. application Ser. No. 07/966,775, filed on Oct. 27, 1992, now abandoned, which is a continuation-in-part of U.S. application Ser. No. 07/907,224, filed on Jul. 1, 1992, now abandoned, which is a continuation-in-part of U.S. application Ser. No. 07/899,660, filed on Jun. 15, 1992, now abandoned, which is a continuation-in-part of U.S. application Ser. No. 07/892,459, filed on Jun. 2, 1992, now abandoned, which is a continuation-in-part of U.S. application Ser. No. 07/889,717, filed on May 26, 1992, now abandoned. Priority is also claimed from International Application PCT/US93/04926.

BACKGROUND OF THE INVENTION

Hodgkin's Disease is a human lymphoma, the etiology of which is still not well understood. The neoplastic cells of Hodgkin's Disease are known as Hodgkin and Reed-Sternberg (H-RS) cells. CD30 is a 120 kd surface antigen widely used as a clinical marker for Hodgkin's lymphoma and related hematologic malignancies (Froese et al., *J. Immunol.* 139:2081 (1987); Pfreundschuh et al., *Onkologie* 12:30 (1989); Carde et al., *Eur. J. Cancer* 26:474 (1990)). Originally identified by the monoclonal antibody Ki-1, which is reactive with H-RS cells (Schwab et al., *Nature* (London) 299:65 (1982)), CD30 was subsequently shown to be expressed on a subset of non-Hodgkin's lymphomas (NHL), including Burkitt's lymphoma, as well as several virally-transformed lines (human T-Cell Lymphotrophic Virus I or II transformed T-cells, and Epstein-Barr Virus transformed B-cells (Stein et al., *Blood* 66:848 (1985); Andreesen et al., *Blood* 63:1299 (1984)). That CD30 plays a role in normal lymphoid interactions is suggested by its histological detection on a small population of lymphoid cells in reactive lymph nodes, and by induced expression on purified T- and B-cells following lectin activation (Stein et al., *Int. J. Cancer* 30:445 (1982) and Stein et al., 1985, supra).

CD30 expression has also been detected on various non-Hodgkin's lymphomas (NHL), such as large-cell anaplastic lymphomas (LCAL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and centroblastic/centrocytic (cb/cc) follicular lymphomas (Stein et al., *Blood* 66:848 (1985); Miettinen, *Arch. Pathol. Lab. Med.* 116:1197 (1992); Piris et al., *Histopathology* 17:211 (1990); Burns et al., *Am. J. Clin. Pathol.* 93:327 (1990); Piris et al., *Histopathology* 18:25 (1991); Eckert et al., *Am. J. Dermatopathol.* 11:345 (1989); Gianotti et al., *Am. J. Dermatopathol.* 13:503 (1991); Maeda et al., *Br. J. Dermatol.* 121:603 (1989)). The association of the CD30 antigen with lymphoid malignancies has proven to be a useful marker for the identification of malignant cells within lymphoid tissues, particularly lymph nodes. However, expression of CD30 has also been reported on a portion of embryonal carcinomas, nonembryonal carcinomas, malignant melanomas, mesenchymal tumors, and myeloid cell lines and macrophages at late stages of differentiation (Schwarting et al., *Blood* 74:1678 (1989); Pallesen et al., *Am J. Pathol.* 133:446 (1988); Mechtersheimer et al., *Cancer* 66:1732 (1990); Andreesen et al., *Am. J. Pathol.* 134:187 (1989)).

Cloning and expression of a gene encoding CD30 has been reported and CD30 has been characterized as a transmembrane protein that possesses substantial homology to the nerve growth factor receptor superfamily (Durkop et al., *Cell* 68:421, 1992). Durkop et al. suggest that CD30 is the receptor for one or more as yet unidentified growth factors, and recognize the importance of investigating the existence and nature of such growth factors in order to achieve insight into the etiology of Hodgkin's Disease.

Prior to the present invention, however, no such growth factors or other molecules that bind to the CD30 receptor were known. A need thus remained for identification and characterization of a ligand for CD30.

SUMMARY OF THE INVENTION

The present invention provides a novel cytokine designated CD30-L, as well as isolated DNA encoding CD30-L protein, expression vectors comprising the isolated DNA, and a method for producing CD30-L by cultivating host cells containing the expression vectors under conditions appropriate for expression of the CD30-L protein. CD30-L is a ligand that binds to the Hodgkin's disease-associated antigen CD30 (a cell surface receptor). Antibodies directed against the CD30-L protein or an immunogenic fragment thereof are also provided. Uses of CD30-L in diagnostic and therapeutic procedures are also disclosed.

DETAILED DESCRIPTION OF THE INVENTION cDNA encoding a novel polypeptide that can act as a ligand for the Hodgkin's Disease-associated receptor known as CD30 has been isolated in accordance with the present invention. Also provided are expression vectors comprising the CD30 ligand (CD30-L) cDNA and methods for producing recombinant CD30-L polypeptides by cultivating host cells containing the expression vectors under conditions appropriate for expression of CD30-L, and recovering the expressed CD30-L. Purified CD30-L protein is also encompassed by the present invention.

The present invention also provides CD30-L or antigenic fragments thereof that can act as immunogens to generate antibodies specific to the CD30-L immunogens. Monoclonal antibodies specific for CD30-L or antigenic fragments thereof thus can be prepared.

The novel cytokine disclosed herein is a ligand for CD30, a receptor that is a member of the TNF/NGF receptor superfamily. Therefore, CD30-L is likely to be responsible for transducing a biological signal via CD30, which is known to be expressed on the surface of Hodgkin's Disease tumor cells.

One use of the CD30 ligand of the present invention is as a research tool for studying the pathogenesis of Hodgkin's Disease. As described in examples 8 and 13, CD30-L enhances the proliferation of the $CD30^+$ neoplastic Hodgkin's Disease-derived lymphoma cell lines HDLM-2 and L-540, which are phenotypically T-cell-like. CD30-L did not produce a detectable effect on proliferation or viability of the B-cell-like, $CD30^+$ Hodgkin's Disease-derived lymphoma cell lines KM-H2 and L-428. The CD30-L of the present invention provides a means for investigating the roles that CD30-L and the cognate receptor may play in the etiology of Hodgkin's Disease.

CD30-L reduced proliferation of $CD30^+$ large cell anaplastic lymphoma cell lines (one type of non-Hodgkin's lymphoma) (see examples 8 and 13). Thus, CD30-L has potential use as a therapeutic agent. CD30-L also finds use in delivering diagnostic or therapeutic agents attached thereto to cells (e.g., malignant cells) that express the CD30 antigen.

The CD30 ligand also induces proliferation of T cells in the presence of an anti-CD3 co-stimulus. The CD30-L of the present invention thus is also useful as a research tool for elucidating the roles that CD30 and CD30-L may play in the immune system. The inducible expression of CD30-L on normal T cells and macrophages, and the presence of its receptor on activated T and B cells, is consistent with both autocrine and paracrine effects.

Upregulation of CD30 accompanying EBV, HTLVI and HTLVII transformation also warrants further investigation, and the CD30-L provided herein is useful in such studies. HTLVI is the proximal cause of adult T cell Leukemia/Lymphoma. EBV has long been associated with Burkitt's lymphoma and nasopharyngeal carcinoma, and, overall, 50% of Hodgkin's lymphomas are $EBV^+$ (reviewed in Klein, *Blood* 80:299 (1992).

The CD30-L polypeptides of the present invention also may be employed in in vitro assays for detection of CD30 or CD30-L or the interactions thereof. Additional cell types expressing CD30 may be identified, for example.

The term "CD30-L" as used herein refers to a genus of polypeptides which are capable of binding CD30. Human CD30-L is within the scope of the present invention, as are CD30-L proteins derived from other mammalian species. As used herein, the term "CD30-L" includes membrane-bound proteins (comprising a cytoplasmic domain, a transmembrane region, and an extracellular domain) as well as truncated proteins that retain the CD30-binding property. Such truncated proteins include, for example, soluble CD30-L comprising only the extracellular (receptor binding) domain.

Isolation of a cDNA encoding murine CD30-L is described in examples 1–4 below. A human CD30-Fc fusion protein was prepared as described in example 1 for use in screening clones in a direct expression cloning procedure, to identify those expressing a protein that binds CD30.

Briefly, total RNA was isolated from a virally transformed human T-cell line designated HUT-102, which has been described by Durkop et al., supra, and Poiesz et al. (*PNAS USA* 77:7415–19, 1980). First strand cDNA was prepared using the total RNA as template. DNA encoding the extracellular domain of human CD30 was amplified by polymerase chain reaction (PCR) using primers based on the human CD30 sequence published by Durkop et al., supra., and the amplified DNA fragment was isolated. An expression vector comprising the CD30 extracellular domain DNA fused in-frame to the N-terminus of a human IgG1 Fc region DNA sequence was constructed and transfected into mammalian cells. The expressed protein was purified by a procedure that involved use of a protein G column (to which the Fc portion of the fusion protein binds).

Three activated murine helper T-cell lines were screened using a fluorescence activated cell sorting technique, and all three were found to bind a fluorescent derivative of the CD30-Fc protein. A cDNA library was prepared from one of the murine helper T-cell lines. cDNA from this library (in a mammalian expression vector that also replicates in *E. coli*) was transfected into COS-7 (mammalian) cells, for isolation of clones expressing a CD30-binding protein by using a direct expression cloning technique. The clones were screened for ability to bind $^{125}I$-CD30/Fc, and a positive clone was isolated. The recombinant vector isolated from the positive clone (murine CD30-L cDNA in plasmid pDC202) was transformed into *E. coli* cells, deposited with the American Type Culture Collection on May 28, 1992, and assigned accession no. ATCC 69004. The deposit was made under the terms of the Budapest Treaty.

The murine CD30-L cDNA was radiolabeled and used as a probe to isolate human CD30-L cDNA by cross-species hybridization. Briefly, a cDNA library prepared from activated human peripheral blood lymphocytes was screened with $^{32}P$-labeled murine cDNA and a positive clone was isolated as described in Example 6. Human CD30-L DNA isolated from the positive clone was inserted into plasmid pGEMBL and then transformed into *E. coli* cells as described in Example 6. Samples of *E. coli* cells transformed with the recombinant vector were deposited with the American Type Culture Collection on Jun. 24, 1992, and assigned accession no. ATCC 69020. The deposit was made under the terms of the Budapest Treaty.

Additional murine and human CD30-L DNA sequences were isolated as described in example 7. The proteins encoded by the clones of example 7 comprise additional amino acids at the N-terminus, compared to the clones isolated in examples 4 and 6.

CD30-L proteins of the present invention thus include, but are not limited to, murine CD30-L proteins characterized by the N-terminal amino acid sequence Met-Gln-Val-Gln-Pro-Gly-Ser-Val-Ala-Ser-Pro-Trp (amino acids 1–12 of SEQ ID NO:19) or Met-Glu-Pro-Gly-Leu-Gln-Gln-Ala-Gly-Ser-Cys-Gly (amino acids 1–12 of SEQ ID NO:6). Human CD30-L proteins characterized by the N-terminal amino acid sequence Met-His-Val-Pro-Ala-Gly-Ser-Val-Ala-Ser-His-Leu (amino acids 1–12 of SEQ ID NO:23) or Met-Asp-Pro-Gly-Leu-Gln-Gln-Ala-Leu-Asn-Gly-Met (amino acids 1–12 of SEQ ID NO:8) also are provided.

While a CD30/Fc fusion protein was employed in the screening procedure described in example 4 below, labeled CD30 could be used to screen clones and candidate cell lines for expression of CD30-L proteins. The CD30/Fc fusion protein offers the advantage of being easily purified. In addition, disulfide bonds form between the Fc regions of two separate fusion protein chains, creating dimers. The dimeric CD30/Fc receptor was chosen for the potential advantage of higher affinity binding of the CD30 ligand, in view of the possibility that the ligand being sought would be multimeric.

Further, other suitable fusion proteins comprising CD30 may be substituted for CD30/Fc in the screening procedures. Other fusion proteins can be made by fusing a DNA sequence for the ligand binding domain of CD30 to a DNA sequence encoding another polypeptide that is capable of affinity purification, for example, avidin or streptavidin. The resultant gene construct can be introduced into mammalian cells to express a fusion protein. Receptor/avidin fusion proteins can be purified by biotin affinity chromatography. The fusion protein can later be recovered from the column by eluting with a high salt solution or another appropriate buffer. Other antibody Fc regions may be substituted for the human IgG1 Fc region described in example 1. Other suitable Fc regions are defined as any region that can bind with high affinity to protein A or protein G, and include the Fc region of murine IgG1 or fragments of the human IgG1 Fc region, e.g., fragments comprising at least the hinge region so that interchain disulfide bonds will form.

cDNA encoding a CD30-L polypeptide may be isolated from other mammalian species by procedures analogous to those employed in isolating the murine CD30-L clone. For example, a cDNA library derived from a different mammalian species may be substituted for the murine cDNA library that was screened for binding of radioiodinated human CD30/Fc fusion protein in the direct expression cloning procedure described in example 4. Cell types from which cDNA libraries may be prepared may be chosen by the FACS selection procedure described in example 2, or any other suitable technique. As one alternative, mRNAs isolated from various cell lines can be screened by Northern hybridization to determine a suitable source of mammalian CD30-L mRNA for use in cloning a CD30-L gene.

Alternatively, one can utilize the murine or human CD30-L cDNAs described herein to screen cDNA derived from other mammalian sources for CD30-L cDNA using cross-species hybridization techniques. Briefly, an oligonucleotide based on the nucleotide sequence of the coding region (preferably the extracellular region) of the murine or human clone, or, preferably, the full length CD30-L cDNA, is prepared by standard techniques for use as a probe. The murine or human probe is used to screen a mammalian cDNA library or genomic library, generally under moderately stringent conditions.

CD30-L proteins of the present invention include, but are not limited to, murine CD30-L comprising amino acids 1–220 of SEQ ID NO:19 or 1–239 of SEQ ID NO:6; human CD30-L comprising amino acids 1–215 of SEQ ID NO:23 or 1–234 of SEQ ID NO:8; and proteins that comprise N-terminal, C-terminal, or internal truncations of the foregoing sequences, but retain the desired biological activity. Examples include murine CD30-L proteins comprising amino acids x to 239 of SEQ ID NO:6, wherein x is 1–19 (i.e., the N-terminal amino acid is selected from amino acids 1–19 of SEQ ID NO:6, and the C-terminal amino acid is amino acid 239 of SEQ ID NO:6.) As described in example 7, amino acids 1–19 of the SEQ ID NO:6 sequence are not essential for binding of murine CD30-L to the CD30 receptor. Also provided by the present invention are human CD30-L proteins comprising amino acids y to 234 of SEQ ID NO:8 wherein y is 1–19 (i.e., the N-terminal amino acid is any one of amino acids 1–19 of SEQ ID NO:8, and amino acid 234 is the C-terminal amino acid. Such proteins, truncated at the N-terminus, are capable of binding CD30, as discussed in example 7.

One embodiment of the present invention provides soluble CD30-L polypeptides. Soluble CD30-L polypeptides comprise all or part of the extracellular domain of a native CD30-L but lack the transmembrane region that would cause retention of the polypeptide on a cell membrane. Since the CD30-L protein lacks a signal peptide, a heterologous signal peptide is fused to the N-terminus of a soluble CD30-L protein to promote secretion thereof, as described in more detail below. The signal peptide is cleaved from the CD30-L protein upon secretion from the host cell. The soluble CD30-L polypeptides that may be employed retain the ability to bind the CD30 receptor. Soluble CD30-L may also include part of the transmembrane region or part of the cytoplasmic domain or other sequences, provided that the soluble CD30-L protein is capable of being secreted.

Soluble CD30-L may be identified (and distinguished from its non-soluble membrane-bound counterparts) by separating intact cells which express the desired protein from the culture medium, e.g., by centrifugation, and assaying the medium (supernatant) for the presence of the desired protein. The culture medium may be assayed using procedures which are similar or identical to those described in the examples below. The presence of CD30-L in the medium indicates that the protein was secreted from the cells and thus is a soluble form of the desired protein.

The use of soluble forms of CD30-L is advantageous for certain applications. Purification of the proteins from recombinant host cells is facilitated, since the soluble proteins are secreted from the cells.

Examples of soluble CD30-L polypeptides include those comprising the entire extracellular domain of a native CD30-L protein or a fragment of said extracellular domain that is capable of binding CD30. One such soluble CD30-L comprises amino acids 49 (Gln) through 220 (Asp) of the murine CD30-L sequence of SEQ ID NO:19. Other soluble CD30-L polypeptides comprise amino acids z to 215 (Asp) of the human CD30-L sequence of SEQ ID NO:23, wherein z is 44, 45, 46, or 47. In other words, the N-terminal amino acid of the soluble human CD30-L is selected from the amino acids in positions 44–47 of SEQ ID NO:23. DNA sequences encoding such soluble human CD30-L polypeptides include, but are not limited to, DNA sequences comprising a nucleotide sequence selected from the group consisting of nucleotides 130–645, 133–645, 136–645, and 139–645 of SEQ ID NO:22. Such sequences encode polypeptides comprising amino acids 44–215, 45–215, 46–215, and 47–215, respectively, of SEQ ID NO:23. Production of one such soluble human CD30-L protein, in the form of a fusion protein comprising amino acids 47–215 of SEQ ID NO:23 and an antibody Fc polypeptide, is illustrated in example 11.

Truncated CD30-L, including soluble polypeptides, may be prepared by any of a number of conventional techniques. In the case of recombinant proteins, a DNA fragment encoding a desired fragment may be subcloned into an expression vector. Alternatively, a desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to isolate a DNA sequence encoding a desired protein fragment.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

The present invention provides purified CD30-L polypeptides, both recombinant and non-recombinant. Variants and derivatives of native CD30-L proteins that retain the desired biological activity are also within the scope of the present invention. CD30-L variants may be obtained by mutations of nucleotide sequences coding for native CD30-L polypeptides. A CD30-L variant, as referred to herein, is a polypeptide substantially homologous to a native CD30-L, but which has an amino acid sequence different from that of native CD30-L (human, murine or other mammalian species) because of one or a plurality of deletions, insertions or substitutions.

The variant amino acid sequence preferably is at least 80% identical to a native CD30-L amino acid sequence, most preferably at least 90% identical. The degree of homology (percent identity) may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making such alterations are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462, which are incorporated by reference herein.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

CD30-L also may be modified to create CD30-L derivatives by forming covalent or aggregative conjugates with other chemical moieties, such as glycosyl groups, lipids, phosphate, acetyl groups and the like. Covalent derivatives of CD30-L may be prepared by linking the chemical moieties to functional groups on CD30-L amino acid side chains or at the N-terminus or C-terminus of a CD30-L polypeptide or the extracellular domain thereof. Other derivatives of CD30-L within the scope of this invention include covalent or aggregative conjugates of CD30-L or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a soluble CD30-L polypeptide. The signal or leader peptide co-translationally or post-translationally directs transfer of the conjugate from its site of synthesis to a site inside or outside of the cell membrane or cell wall.

CD30-L polypeptide fusions can comprise peptides added to facilitate purification and identification of CD30-L. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK) (SEQ ID NO:15), which is highly antigenic and provides an epitope reversibly bound by a specific monoclonal antibody enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. A murine hybridoma designated 4E11 produces a monoclonal antibody that binds the peptide DYKDDDDK (SEQ ID NO:15) in the presence of certain divalent metal cations (as described in U.S. Pat. No. 5,011,912) and has been deposited with the American Type Culture Collection under accession no HB 9259.

The present invention further includes CD30-L polypeptides with or without associated native-pattern glycosylation. CD30-L expressed in yeast or mammalian expression systems (e.g., COS-7 cells) may be similar to or significantly different from a native CD30-L polypeptide in molecular weight and glycosylation pattern, depending upon the choice of expression system. Expression of CD30-L polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, N-glycosylation sites in the CD30-L extracellular domain can be modified to preclude glycosylation while allowing expression of a homogeneous, reduced carbohydrate analog using yeast or mammalian expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846.

In another example, sequences encoding Cys residues that are not essential for biological activity can be altered to cause the Cys residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The resulting muteins are less susceptible to cleavage by the KEX2 protease at locations other than the yeast α-factor leader sequence, where cleavage upon secretion is intended.

Naturally occurring CD30-L variants are also encompassed by the present invention. Examples of such variants are proteins that result from alternative mRNA splicing events (since CD30-L presumably is encoded by a multi-exon gene) or from proteolytic cleavage of the CD30-L protein, wherein the CD30-binding property is retained. Alternative splicing of mRNA may yield a truncated but biologically active CD30-L protein, such as a naturally occurring soluble form of the protein, for example. Variations attributable to proteolysis include, for example, differences in the N- or C-termini upon expression in different types of host cells, due to proteolytic removal of one or more terminal amino acids from the CD30-L protein (generally from 1–5 terminal amino acids).

Nucleic acid sequences within the scope of the present invention include isolated DNA and RNA sequences that hybridize to the CD30-L nucleotide sequences disclosed herein under conditions of moderate or severe stringency, and which encode biologically active CD30-L. Moderate stringency hybridization conditions refer to conditions described in, for example, Sambrook et al. *Molecular Cloning: A Laboratory Manual*, 2 ed. Vol. 1, pp. 1.101–104, Cold Spring Harbor Laboratory Press, (1989). Conditions of moderate stringency, as defined by Sambrook et al., include use of a prewashing solution of 5×SSC, 0.5% SDS, 1.0 mM EDTA (pH 8.0) and hybridization conditions of about 55° C., 5×SSC, overnight. Conditions of severe stringency include higher temperatures of hybridization and washing. The skilled artisan will recognize that the temperature and wash solution salt concentration may be adjusted as necessary according to factors such as the length of the probe. One embodiment of the invention is directed to DNA sequences that will hybridize under severely stringent conditions to a DNA sequence comprising the coding region of a CD30-L clone disclosed herein. The severely stringent conditions include hybridization at 68° C. followed by washing in 0.1×SSC/0.1% SDS at 63–68° C.

The present invention thus provides isolated DNA sequences encoding biologically active CD30-L, selected from: (a) DNA derived from the coding region of a native mammalian CD30-L gene (e.g., DNA comprising the nucleotide sequence presented in SEQ ID NOS:5, 7, 18, or 22; (b) DNA capable of hybridization to a DNA of (a) under moderately (or severely) stringent conditions and which encodes biologically active CD30-L; and (c) DNA which is degenerate as a result of the genetic code to a DNA defined in (a) or (b) and which encodes biologically active CD30-L. CD30-L proteins encoded by the DNA sequences of (a), (b) and (c) are encompassed by the present invention.

Examples of CD30-L proteins encoded by DNA that varies from the native DNA sequences of SEQ ID NOS:5, 7, 18, or 22, wherein the variant DNA will hybridize to a native DNA sequence under moderately stringent conditions, include, but are not limited to, CD30-L fragments (soluble or membrane-bound) and CD30-L proteins comprising inactivated N-glycosylation site(s), inactivated KEX2 protease processing site(s), or conservative amino acid substitution (s), as described above. CD30-L proteins encoded by DNA derived from other mammalian species, wherein the DNA will hybridize to the human or murine DNA of SEQ ID NOS:5, 7, 18, or 22, are also encompassed.

Variants possessing the requisite ability to bind CD30 may be identified by any suitable assay. Biological activity of CD30-L may be determined, for example, by competition for binding to the ligand binding domain of CD30 (i.e. competitive binding assays).

One type of a competitive binding assay for CD30-L polypeptide uses a radiolabeled, soluble human or murine CD30-L and intact cells expressing cell surface CD30 (e.g., cell lines such as HUT102, described by Durkop et al., supra). Instead of intact cells, one could substitute soluble CD30 bound to a solid phase (such as a CD30/Fc fusion protein bound to a Protein A or Protein G column through interaction with the Fc region of the fusion protein). Another type of competitive binding assay utilizes radiolabeled soluble CD30 such as a CD30/Fc fusion protein, and intact cells expressing CD30-L. Alternatively, soluble CD30-L could be bound to a solid phase.

Competitive binding assays can be performed using standard methodology. For example, radiolabeled murine CD30-L can be used to compete with a putative CD30-L homolog to assay for binding activity against surface-bound CD30. Qualitative results can be obtained by competitive autoradiographic plate binding assays, or Scatchard plots may be utilized to generate quantitative results.

Competitive binding assays with intact cells expressing CD30 can be performed by two methods. In a first method, cells expressing cell surface CD30 are grown either in suspension or by adherence to tissue culture plates. Adherent cells can be removed by treatment with 5 mM EDTA treatment for ten minutes at 37° C. In a second method, transfected COS cells expressing membrane-bound CD30 can be used. COS cells or another mammalian cell can be transfected with human CD30 cDNA in an appropriate vector to express full length CD30 with an extracellular region.

Alternatively, soluble CD30 can be bound to a solid phase such as a column chromatography matrix or a similar substrate suitable for analysis for the presence of a detectable moiety such as $^{125}I$. Binding to a solid phase can be accomplished, for example, by obtaining a CD30/Fc fusion protein and binding it to a protein A or protein G-containing matrix.

Another means to measure the biological activity of CD30-L (including variants) is to utilize conjugated, soluble CD30(for example, $^{125}I$-CD30/Fc) in competition assays similar to those described above. In this case, however, intact cells expressing CD30-L, or soluble CD30-L bound to a solid substrate, are used to measure competition for binding of labeled, soluble CD30 to CD30-L by a sample containing a putative CD30-L variant.

The CD30-L of the present invention can be used in a binding assay to detect cells expressing CD30. For example, CD30-L or an extracellular domain or a fragment thereof can be conjugated to a detectable moiety such as $^{125}I$ Radiolabeling with $^{125}I$ can be performed by any of several standard methodologies that yield a functional $^{125}I$-CD30-L molecule labeled to high specific activity. Alternatively, another detectable moiety such as an enzyme that can catalyze a colorometric or fluorometric reaction, biotin or avidin may be used. Cells to be tested for CD30 expression can be contacted with conjugated CD30-L. After incubation, unbound conjugated CD30-L is removed and binding is measured using the detectable moiety.

The CD30 ligand proteins disclosed herein also may be employed to measure the biological activity of CD30 protein in terms of binding affinity for CD30-L. To illustrate, CD30-L may be employed in a binding affinity study to measure the biological activity of a CD30 protein that has been stored at different temperatures, or produced in different cell types. The biological activity of a CD30 protein thus can be ascertained before it is used in a research study, for example.

CD30-L proteins find use as reagents that may be employed by those conducting "quality assurance" studies, e.g., to monitor shelf life and stability of CD30 protein under different conditions. CD30 ligands may be used in determining whether biological activity is retained after modification of a CD30 protein (e.g., chemical modification, truncation, mutation, etc.). The binding affinity of the modified CD30 protein for a CD30-L is compared to that of an unmodified CD30 protein to detect any adverse impact of the modifications on biological activity of CD30.

A different use of a CD30 ligand is as a reagent in protein purification procedures. CD30-L or CD30-L/Fc fusion proteins may be attached to a solid support material by conventional techniques and used to purify CD30 by affinity chromatography.

CD30-L polypeptides also find use as carriers for delivering agents attached thereto to cells bearing the CD30 cell surface antigen. As discussed above, CD30 has been detected on cells that include, but are not limited to, cells associated with various lymphoid malignancies, e.g., Hodgkin's Disease tumor cells and certain non-Hodgkin's lymphoma cells, e.g., large cell anaplastic lymphoma (LCAL) cells. $CD30^+$ LCALs are characterized by the presence of strong CD30 surface expression on the anaplastic lymphoma cells (Stein et al., *Blood* 66:848, 1985). CD30-L polypeptides thus can be used to deliver diagnostic or therapeutic agents to these cells (or to other cell types found to express CD30 on the cell surface) in in vitro or in vivo procedures. $CD30^+$ cells are contacted with a conjugate comprising a diagnostic or therapeutic agent attached to a CD30-L polypeptide. The CD30-L binds to the target cells, thus allowing detection thereof (in the case of diagnostic agents) or treatment thereof (with therapeutic agents).

One example of such use is to expose a $CD30^+$ lymphoma cell line to a therapeutic agent/CD30-L conjugate to assess whether the agent exhibits cytotoxicity toward the lymphoma cells. A number of different therapeutic agents attached to CD30-L may be included in an assay to detect and compare the cytotoxic effects of the agents on the lymphoma cells. CD30-L/diagnostic agent conjugates may be employed to detect the presence of $CD30^+$ cells in vitro or in vivo.

Diagnostic and therapeutic agents that may be attached to a CD30-L polypeptide include, but are not limited to, drugs, toxins, radionuclides, chromophores, enzymes that catalyze a colorimetric or fluorometric reaction, and the like, with the particular agent being chosen according to the intended application. Examples of drugs include those used in treating various forms of cancer, e.g., mechlorethamine, procarbazine, prednisone, dacarbazine, nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine or vinblastine, and antibiotics such as calicheamycin, bleomycin, doxorubicin, daunorubicin, and derivatives thereof. Combinations of such drugs, attached to CD30-L, may be employed. Among the toxins are ricin, abrin, saporin toxin, diptheria toxin. *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}I$, $^{131}I$, $^{99m}Tc$, $^{111}In$, and $^{76}Br$. Radionuclides suitable for therapeutic use include, but are not limited to, $^{131}I$, $^{211}At$, $^{77}Br$, $^{186}Re$, $^{188}Re$, $^{212}Pb$, 212Bi, $^{109}Pd$, $^{64}Cu$, and $^{67}Cu$.

Such agents may be attached to the CD30-L by any suitable conventional procedure. CD30-L, being a protein, comprises functional groups on amino acid side chains that can be reacted with functional groups on a desired agent to form covalent bonds, for example. The agent may be covalently linked to CD30-L via an amide bond, hindered disulfide bond, acid-cleavable linkage, and the like, which are among the conventional linkages chosen according to such factors as the structure of the desired agent. Alternatively, CD30-L or the agent to be linked thereto may be derivatized to generate or attach a desired reactive functional group. The derivatization may involve attachment of one of the bifunctional coupling reagents available for linking various molecules to proteins (Pierce Chemical Company, Rockford, Ill.). A number of techniques for radiolabeling proteins are known. One such method involves use of the IODO-GEN reagent (Pierce Chemical Company) to radioiodinate a CD30-L polypeptide. Radionuclide metals may be attached to CD30-L by using a suitable bifunctional chelating agent, examples of which are described in U.S. Pat. Nos. 4,897,255 and 4,965,392.

Conjugates comprising CD30-L and a suitable diagnostic or therapeutic agent (preferably covalently linked) are thus prepared. The conjugates are administered or otherwise employed in an amount appropriate for the particular application.

Preferred therapeutic agents are radionuclides and drugs. In one embodiment of the invention, the anti-tumor drug calicheamycin is attached to a soluble human CD30 ligand polypeptide.

As illustrated in examples 8 and 13, CD30 ligand polypeptides of the present invention have been found to reduce proliferation of LCAL cell lines. The CD30-L was employed in unlabeled form, i.e., did not have any therapeutic agent attached thereto. Thus, one embodiment of the present invention is directed co a method for inhibiting proliferation of $CD30^+$ LCAL cells by contacting said cells with a CD30-L polypeptide. The present invention further provides a method for treating LCAL, involving administering a therapeutically effective amount of a CD30-L polypeptide to a patient afflicted with LCAL.

Hybridoma cell lines that produce two monoclonal antibodies (MAbs) designated M44 and M67 were generated as described in example 12, using a soluble human CD30/Fc fusion protein as the immunogen. The M44 and M67 MAbs exhibited certain biological activities in common with CD30-L, one of which is reduction of proliferation of LCAL cells. Thus, the present invention also provides a method of inhibiting proliferation of $CD30^+$ LCAL cells by contacting said cells with M44, M67, or a combination thereof. The M44 or M67 antibodies may be substituted for CD30-L in the above-described method for treating LCAL patients. M44 and M67 are also useful for delivering diagnostic or cytotoxic agents attached thereto to any $CD30^+$ cells. "Humanized" or chimeric versions of these antibodies (e.g., comprising a human constant region), may be produced by known techniques and employed in the foregoing methods. Antigen-binding antibody fragments (e.g., Fab, Fab', or $F(ab')_2$ fragments) also may be employed.

Oligomeric Forms of CD30-L

CD30-L polypeptides may exist as oligomers, such as dimers or trimers. Oligomers may be linked by disulfide bonds formed between cysteine residues on different CD30-L polypeptides. In one embodiment of the invention, a CD30-L dimer is created by fusing CD30-L to the Fc region of an antibody (IgG1) in a manner that does not interfere with binding of CD30-L to the CD30 ligand binding domain. The Fc polypeptide preferably is fused to the N-terminus of a soluble CD30-L (comprising only the extracellular domain). A procedure for isolating DNA encoding an IgG1 Fc region for use in preparing fusion proteins is presented in example 1 below. A gene fusion encoding the CD30-L/Fc fusion protein is inserted into an appropriate expression vector. The CD30-L/Fc fusion proteins are allowed to assemble much like antibody molecules, whereupon interchain disulfide bonds form between Fc polypeptides, yielding divalent CD30-L. If fusion proteins are made with both heavy and light chains of an antibody, it is possible to form a CD30-L oligomer with as many as four CD30-L extracellular regions.

Alternatively, one can link multiple copies of CD30-L via peptide linkers. A fusion protein comprising two or more copies of CD30-L (preferably soluble CD30-L polypeptides), separated by peptide linkers, may be produced by recombinant DNA technology. Among the peptide linkers that may be employed are amino acid chains that are from 5 to 100 amino acids in length, preferably comprising amino acids selected from the group consisting of glycine, asparagine, serine, threonine, and alanine. The production of recombinant fusion proteins comprising peptide linkers is illustrated in U.S. Pat. No. 5,073,627, for example, which is hereby incorporated by reference.

The present invention provides oligomers of CD30-L extracellular domains or fragments thereof, linked by disulfide bonds, or expressed as fusion proteins with or without spacer amino acid linking groups. For example, a dimer CD30-L molecule can be linked by an IgG Fc region linking group. Analysis of expressed recombinant CD30-L of the present invention by SDS-PAGE revealed both monomeric and oligomeric forms of the protein. The CD30-L proteins of the present invention are believed to form oligomers (disulfide-bonded dimers, trimers and higher oligomers) intracellularly. The oligomers then become attached to the cell surface via the transmembrane region of the protein.

Expression Systems

The present invention provides recombinant expression vectors for expression of CD30-L, and host cells transformed with the expression vectors. Any suitable expression system may be employed. The vectors include a CD30-L DNA sequence (e.g., a synthetic or cDNA-derived DNA sequence encoding a CD30-L polypeptide) operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the CD30-L DNA sequence. Thus, a promoter nucleotide sequence is operably linked to a CD30-L DNA sequence if the promoter nucleotide sequence controls the transcription of the CD30-L DNA sequence. The ability to replicate in the desired host cells, usually conferred by an origin of replication, and a selection gene by which transformants are identified, may additionally be incorporated into the expression vector.

In addition, sequences encoding appropriate signal peptides that are not native to the CD30-L gene can be incorporated into expression vectors. For example, a DNA sequence for a signal peptide (secretory leader) may be fused in frame to the CD30-L sequence so that the CD30-L is initially translated as a fusion protein comprising the signal peptide. A signal peptide fused to the N-terminus of a soluble CD30-L protein promotes extracellular secretion of the CD30-L. The signal peptide is cleaved from the CD30-L polypeptide upon secretion of CD30-L from the cell. Signal peptides are chosen according to the intended host cells, and representative examples are described below.

Suitable host cells for expression of CD30-L polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce CD30-L polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a CD30-L polypeptide may include an N-terminal methionine residue to facilitate expression of the recombinant polypeptide in the prokaryotic host cell. The N-terminal Met may be cleaved from the expressed recombinant CD30-L polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a CD30-L DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis. USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res*. 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

CD30-L alternatively may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2 μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the CD30-L polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant CD30-L polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and PCT Application WO 91/18982, incorporated by reference herein. The vectors may be derived from retroviruses. To achieve secretion of CD30-L (a type II protein lacking a native signal sequence), a heterologous signal sequence may be added. Examples of signal peptides useful in mammalian expression systems are the signal sequence for interleukin-7 (IL-7) described in U.S. Pat. No. 4,965,195; the signal sequence for interleukin-2 receptor described in Cosman et al., *Nature* 312:768 (1984); the interleukin-4 signal peptide described in EP 367,566; the type I interleukin-1 receptor signal peptide described in U.S. Pat. No. 4,968,607; and the type II interleukin-1 receptor signal peptide described in EP 460,846. Each of these references describing signal peptides is hereby incorporated by reference.

CD30 Ligand Protein

The present invention provides substantially homogeneous CD30-L protein, which may be produced by recombinant expression systems as described above or purified from naturally occurring cells. The CD30-L is purified to substantial homogeneity, as indicated by a single protein band upon analysis by SDS-polyacrylamide gel electrophoresis (SDS-PAGE).

In one embodiment of the present invention, CD30-L is purified from a cellular source using any suitable protein purification technique. The cells may, for example, be activated T-lymphocytes from a mammalian species of interest, such as the murine cell line 7B9 described in examples 2 and 3 or induced human peripheral blood T-cells.

An alternative process for producing the CD30-L-protein comprises culturing a host cell transformed with an expression vector comprising a DNA sequence that encodes CD30-L under conditions such that CD30-L is expressed. The CD30-L protein is then recovered from culture medium or cell extracts, depending upon the expression system employed. As the skilled artisan will recognize, procedures for purifying the recombinant CD30-L will vary according to such factors as the type of host cells employed and whether or not the CD-30-L is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify CD30-L. Some or all of the foregoing purification steps, in various combinations, can be employed to provide a substantially homogeneous recombinant protein.

It is also possible to utilize an affinity column comprising the ligand binding domain of CD30 to affinity-purify expressed CD30-L polypeptides. CD30-L polypeptides can be removed from an affinity column in a high salt elution buffer and then dialyzed into a lower salt buffer for use. Alternatively, the affinity column may comprise an antibody that binds CD30-L. Example 5 describes a procedure for employing the CD30-L protein of the present invention to generate monoclonal antibodies directed against CD30-L.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express CD30-L as a secreted polypeptide. This simplifies purification. Secreted recombinant polypeptide from a yeast host cell fermentation can be purified by methods analogous to those disclosed by Urdal et al. (*J. Chromatog*. 296:171, 1984). Urdal et al. describe two sequential, reversed-phase HPLC steps for purification of recombinant human IL-2 on a preparative HPLC column.

The present invention provides pharmaceutical compositions comprising an effective amount of a purified CD30-L polypeptide and a suitable diluent, excipient, or carrier. Such carriers will be nontoxic to patients at the dosages and concentrations employed. Ordinarily, the preparation of such compositions entails combining a mammalian CD30-L polypeptide or derivative thereof with buffers, antioxidants such as ascorbic acid, low molecular weight (less than about 10 residues) peptides, proteins, amino acids, carbohydrates including glucose, sucrose, or dextrans, chelating agents such as EDTA, glutathione, or other stabilizers and excipients. Neutral buffered saline is one appropriate diluent.

For therapeutic use, the compositions are administered in a manner and dosage appropriate to the indication and the patient. As will be understood by one skilled in the pertinent field, a therapeutically effective dosage will vary according to such factors as the nature and severity of the disorder to be treated and the age, condition, and size of the patient. Administration may be by any suitable route, including but not limited to intravenous injection, continuous infusion, local infusion during surgery, or sustained release from implants (gels, membranes, and the like).

The compositions of the present invention may contain a CD30-L protein in any form described above, including variants, derivatives, biologically active fragments, and oligomeric forms thereof. CD30-L derived from the same mammalian species as the patient is generally preferred for use in pharmaceutical compositions. In one embodiment of the invention, the composition comprises a soluble human CD30-L protein. Such protein may be in the form of dimers comprising the extracellular domain of human CD30-L fused to an Fc polypeptide, as described above. In another embodiment of the invention, the pharmaceutical composition comprises a CD30-L polypeptide having a diagnostic or therapeutic agent attached thereto. Such compositions may be administered to diagnose or treat conditions characterized by $CD30^+$ cells, e.g., Hodgkin's Disease or large cell anaplastic lymphomas, as discussed above. A composition comprising unlabeled CD30-L may be used in treating LCAL. The foregoing compositions may additionally contain, or be co-administered with, additional agents effective in treating malignancies characterized by $CD30^+$ cells.

Nucleic Acid Fragments

The present invention further provides fragments of the CD30-L nucleotide sequences presented herein. Such fragments desirably comprise at least about 14 nucleotides of the sequence presented in SEQ ID NO:5 or SEQ ID NO:7. DNA and RNA complements of said fragments are provided herein, alone with both single-stranded and double-stranded forms of the CD30-L DNA Among the uses of such CD30-L nucleic acid fragments is use as a probe. Such probes may be employed in cross-species hybridization procedures to isolate CD30-L DNA from additional mammalian species. As one example, a probe corresponding to the extracellular domain of CD30-L may be employed. The probes also find use in detecting the presence of CD30-L nucleic acids in in vitro assays and in such procedures as Northern and Southern blots. Cell types expressing CD30-L can be identified. Such procedures are well known, and the skilled artisan can choose a probe of suitable length, depending on the particular intended application.

Other useful fragments of the CD30-L nucleic acids are antisense or sense oligonucleotides comprising a single-stranded nucleic acid sequence (either RNA or DNA) capable of binding to target CD30-L mRNA (sense) or CD30-L DNA (antisense) sequences. Antisense or sense oligonucleotides, according to the present invention, comprise a fragment of the coding region of CD30-L cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res*. 48:2659, 1988 and van der Krol et al., *BioTechniques* 6:958, 1988.

Binding of antisense or sense olgionucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of CD30-L proteins.

Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence. Antisense or sense oligonucleotides may be introduced into a cell containing the target nucleic acid sequence by any gene transfer method, including, for example, $CaPO_4$-mediated DNA transfection, electroporation, or other gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT application U.S. Ser. No. 90/02656).

Sense or antisense oligonucleotides may also be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to illustrate particular embodiments and not to limit the scope of the invention.

EXAMPLE 1

Preparation of Soluble CD30/Fc Fusion Protein

This example describes construction of a CD30/Fc-encoding vector to express a soluble CD30/Fc fusion protein for use in detecting cDNA clones encoding a CD30 ligand. A cDNA fragment encoding the extracellular region (ligand binding domain) of the CD30 human receptor was obtained using polymerase chain reaction (PCR) techniques, and is based upon the sequence published by Durkop et al. (*Cell* 68:421, 1992). The CD30 nucleotide sequence reported in Durkop et al. supra is presented in SEQ ID NO:1, and the amino acid sequence encoded thereby is presented in SEQ ID NO:2. The signal sequence comprises amino acids 1–18, and the transmembrane region comprises amino acids 391–407, of SEQ ID NO:2.

The CD30 cDNA used as a template in the PCR reaction was prepared as follows. Total RNA was isolated from a virally transformed human T-cell line designated HUT 102E. This cell line was derived by transforming T-cells with human T-cell lymphotropic virus 1 (HTLV-1) as described by Poiesz et al. (*PNAS USA* 77:7415–19, 1980). First strand cDNA was prepared using a SuperScript™ cDNA synthesis kit available from GIBCO/BRL (Gaithersburg, Md.). The resulting single-stranded cDNA was employed as the template in a PCR reaction.

The 5' primer employed in the PCR reaction was a single-stranded oligonucleotide (39-mer) of the sequence:

5' ATAGCGGCCGCCACC
ATGCGCGTCCTCCTCGCCGCGCTG 3'

This primer (SEQ ID NO:9) comprises a recognition site for the restriction endonuclease NotI (underlined) upstream of a sequence (double underline) encoding the first (N-terminal) eight amino acids of the CD30 sequence shown in SEQ ID NO:1, from methionine (encoded by the translation initiation codon ATG) through leucine at position eight.

The 3' primer employed in the PCR reaction was a single-stranded oligonucleotide (39-mer) of the sequence:

3' CAGCGAGAGAGGAGGTGCCCCTTCCTCGGG
TCTAGAACA 5'

This primer (SEQ ID NO:10) comprises a sequence (double underline) that is complementary to the sequence that encodes the last eight amino acids of the CD30 extracellular domain, i.e., amino acids 372 (Val) through 379 (Lys) shown in SEQ ID NO:1. The sequence CTCGGG that follows the CD30 sequence is complementary to codons for Glu and Pro. Glu and Pro are the first two amino acids of an antibody Fc fragment that is fused to the C-terminus of the CD30 fragment as described below. The primer also positions a recognition site for the restriction endonuclease BglII (underlined) downstream, for use in attaching a DNA sequence encoding the remainder of the Fc-encoding gene.

The PCR reaction may be conducted using any suitable procedure, such as those described in Sarki et al., *Science* 239:487 (1988); in *Recombinant DNA Methodology*, Wu et al., eds., Academic Press Inc., San Diego (1989), pp. 189–196; and in *PCR Protocols: A Guide to Methods and Applications*, Innis et al., eds., Academic Press, Inc. (1990). An example of a suitable PCR procedure is as follows. All temperatures are in degrees centigrade. The following PCR reagents are added to a 0.5 ml Eppendorf microfuge tube: 10 μl of 10×PCR buffer (500 mM KCl, 100 mM Tris-HCl, pH 8.3 at 25° C., 25 mM $MgCl_2$, and 1 mg/ml gelatin) (Perkins-Elmer Cetus, Norwalk, Conn.), 8 μl of a 2.5 mM solution containing each dNTP (2 mM dATP, 2 mM dCTP, 2 mM dGTP and 2 mM dTTP), 2.5 units (0.5 μl of standard 5000 units/ml solution) of Taq DNA polymerase (Perkins-Elmer Cetus), 1 ng of template DNA, 100 picomoles of each of the oligonucleotide primers, and water to a final volume of 100 μl. The final mixture is then overlaid with 100 μl parafin oil. PCR is carried out using a DNA thermal cycler (Ericomp, San Diego, Calif.).

In a preferred procedure, the template was denatured at 94° for 5 minutes, followed by 5 cycles of 94° for 1 minute (denaturation), 48° for 1 min. (annealing), and 72° for 1 min. (extension); followed by 30 cycles of 94° for 1 min., 68° for 1 min., and 72° for 1 min., with the last cycle being followed by a final extension at 72° for 5 mins. An aliquot of the products of this PCR reaction was reamplified in a second PCR reaction, using the same conditions.

The desired DNA fragment amplified by this PCR reaction comprised a NotI site upstream of a sequence encoding the entire extracellular domain of CD30, followed by a BglII site. The PCR reaction products were digested with NotI and BglII, and the desired fragment was purified by gel electrophoresis.

A DNA sequence encoding an antibody Fc fragment, to be fused to the CD30-encoding DNA fragment, was prepared as follows. DNA encoding a single chain polypeptide derived from the Fc region of a human IgG1 antibody has been cloned into the SpeI site of the pBLUESCRIPT SK® vector, which is available from Stratagene Cloning Systems, La Jolla, Calif. This plasmid vector is replicable in *E. coli* and contains a polylinker segment that includes 21 unique restriction sites. The DNA and encoded amino acid sequences of the cloned Fc cDNA coding region are presented in FIG. 2. A unique BglII site has been introduced near the 5' end of the inserted Fc encoding sequence. Nucleotides 7–12 of SEQ ID NO:1 constitute the BglII recognition sequence.

The Fc polypeptide encoded by the DNA extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate CD30/Fc fusion proteins, forming dimers as discussed above.

The recombinant vector containing the Fc sequence is digested with BglII (which cleaves only at the site shown in FIG. 2) and NotI (which cleaves the vector in the multiple cloning site downstream of the Fc cDNA insert. The Fc-encoding fragment (about 720 bp in length) was isolated by conventional procedures using LMT agarose gel electrophoresis.

The NotI/BglII CD30-encoding DNA fragment and the BglII/NotI Fc-encoding DNA fragment prepared above were ligated into an expression vector designated pDC406 as follows. Plasmid pDC406, which has been described by McMahan et al. (*EMBO J*. 10:2821, 1991), is an expression vector for use in mammalian cells, but is also replicable in *E. coli* cells.

pDC406 contains origins of replication derived from SV40, Epstein-Barr virus and pBR322 and is a derivative of HAV-EO described by Dower et al., *J. Immunol.* 142:4314 (1989). pDC406 differs from HAV-EO by the deletion of the intron present in the adenovirus 2 tripartite leader sequence in HAV-EO. pDC406 was digested with NotI, which cleaves the plasmid in a multiple cloning site just 3' of the SalI site, then treated with calf intestine alkaline phosphatase (CIAP) to prevent self ligation.

A three-way ligation to join the vector, Fc, and CD30 DNA fragments was conducted under conventional conditions, and *E. coli* cells were transformed with the ligation mixture. A plasmid of the desired size that was recovered from the *E. coli* cells was found to comprise the CD30/Fc gene fusion insert, but in the wrong orientation for expression. The CD30/Fc gene fusion was excised from this recombinant plasmid by NotI digestion and ligated to NotI-digested and CIAP-treated pDC406. *E. coli* cells were transformed with the ligation mixture. A recombinant plasmid containing the insert in the desired orientation was isolated. The CD30 sequence was fused (in the same reading frame) to the downstream Fc sequence.

CD30/Fc fusion molecules preferably are synthesized in recombinant mammalian cell culture because they are generally too large and complex to be synthesized by prokaryotic expression methods. Examples of suitable mammalian cells for expressing a receptor/Fc fusion protein include CV-1 cells (ATCC CCL 70) and COS-7 cells (ATCC CRL 1651), both derived from monkey kidney.

The DNA construct pDC406/CD30/Fc was transfected into the monkey kidney cell line CV-1/EBNA (ATCC CRL 10478). In mammalian host cells such as CV1/EBNA, the CD30/Fc fusion protein is expressed off the HIV transactivating region (TAR) promoter. The CV-1/EBNA cell line was derived by transfection of the CV-1 cell line (ATCC CCL 70) with a gene encoding Epstein-Barr virus nuclear antigen-1 (EBNA-1) that constitutively expresses EBNA-1 driven from the human CMV intermediate-early enhancer/promoter as described by McMahan et al., supra. The EBNA-1 gene allows for episomal replication of expression vectors, such as pDC406, that contain the EBV origin of replication.

CVI-EBNA cells transfected with the pDC406/CD30/Fc vector were cultivated in roller bottles to allow transient expression of the fusion protein, which is secreted into the culture medium via the CD30 signal peptide. The CD30/Fc fusion protein was purified by affinity chromatography. Briefly, one liter of culture supernatant containing the CD30/Fc fusion protein was purified by filtering the supernatants (e.g., in a 0.45 $\mu$ filter) and applying the filtrate to a protein G affinity column (Schleicher and Schuell, Keene, N.H.) according to manufacturer's instructions. The Fc portion of the fusion protein is bound by the Protein G on the column. Bound fusion protein was eluted from the column and the purity confirmed on a silver stained SDS gel.

EXAMPLE 2

Screening of Cell Lines for Binding of CD30

This example describes screening of certain cell lines for the ability to bind a CD30/Fc fusion protein. Those cell lines found to be capable of binding CD30/Fc were considered to be candidates for use as nucleic acid sources in the attempt to clone CD30-L.

Biotinylation of CD30/Fc Fusion Proteins

The purified CD30/Fc fusion protein prepared in Example 1 was labeled with biotin for use in screening cell lines. CD30/Fc or control human IL-4R/Fc were biotinylated as follows: 50 $\mu$g protein (200–500 $\mu$g/ml in 0.1M $NaHCO_3$ pH 8.3) was incubated with 2 $\mu$g (1 mg/ml in DMSO) Biotin-X-N-hydroxysuccinimide (NHS, Calbiochem, La Jolla, Calif.) for 30 min at room temperature. At the end of the incubation period, the reaction mixture was microfuged through a 1 ml Sephadex G-25 (Pharmacia) desalting column and the eluate adjusted to 100 $\mu$g/ml in PBS plus 0.02% $NaN_3$. Protein concentration of biotinylated CD30/Fc and hIL4R/Fc was determined by micro-BCA assay (Pierce, Rockford, Ill.) with ultrapure bovine serum albumin as standard.

Flow Cytometric Staining with Biotinylated Fc Fusion Proteins

Cell lines such as those identified below are screened for binding of biotinylated CD30/Fc by the following procedure. Staining of $1\times10^6$ cells was carried out in round-bottomed 96-well microtiter plates in a volume of 20 $\mu$l. Cells were pre-incubated for 30 min at 4° C. with 50 $\mu$l blocking solution consisting of 100 $\mu$g/ml human IgG1+2% goat serum in PBS+azide to prevent non-specific binding of labeled fusion proteins to Fc receptors. 150 $\mu$l PBS+azide was then added to the wells and cells were pelleted by centrifugation for 4 min at 1200 rpm. Pellets were resuspended in 20 $\mu$l of 5 $\mu$g/ml biotinylated CD30/Fc or biotinylated hIL-4R/Fc (as a specificity control) diluted in blocking solution. After 30–45 min incubation at 4° C., cells were washed ×2 in PBS+azide and resuspended in 20 $\mu$l streptavidin-phycoerythrin (Becton Dickinson) diluted 1:5 in PBS+azide. After an additional 30 min, cells are washed ×2 and are ready for analysis. If necessary, stained cells can be fixed in 1% formaldehyde, 1% fetal bovine serum in PBS+azide and stored at 4° C. in the dark for analysis at a later time.

Streptavidin binds to the biotin molecule which was attached to the CD30/Fc protein. Phycoerythrin is a fluorescent phycobiliprotein which serves as a detectable label. The level of fluorescence signal was then measured for each cell type using a FACScan® flow cytometer (Becton Dickinson).

Cell Lines to be Screened for CD30/Fc Binding

Sheep red blood cell (SRBC)-specific helper T-cell lines designated 7C2 (TH1), 7B9 (TH0) and SBE11 (TH2) were derived by limiting dilution from primary antigen-induced cultures of murine C57BL/6 spleen cells. TH phenotypes of these clones were determined by their ability to secrete IL-2 and/or IL-4 in response to stimulation with the mitogen concanavalin A (ConA).

Human peripheral blood T-cells were stimulated for 16 hours with 10 $\mu$g/ml of an anti-CD3 monoclonal antibody immobilized on plastic, prior to assay for CD30/Fc binding. The anti-CD3 MAb stimulates the T-cells through the CD3-T-cell receptor (TCR) complex.

Biotinylated CD30/Fc Binding

Murine T-cell lines 7C2, 7B9 and SBE11 showed significant binding of biotinylated CD30/Fc over that seen with control IL-4R/Fc, after stimulation for 18 hours with 3 $\mu$g/ml Con A. 7C2 cells were also assayed after 6 hours stimulation with Con A, and specific binding of labeled CD30/Fc was seen. The anti-CD3 MAb activated human T-cells showed significant binding of biotinylated CD30/Fc. Binding of biotinylated CD30/Fc was not detected on any of these cell lines in the absence of stimulation.

Any of the cell lines that demonstrated binding of CD30/Fc may be used as a source of nucleic acid in an attempt to isolate a CD30-L-encoding DNA sequence. A cDNA library may be prepared from any of the three Con A stimulated murine T-cell lines or the activated human peripheral blood T-celis, and screened to identity CD30-L cDNA using the direct expression cloning strategy described below, for example. Other types of activated T-cells may be screened for CD30 binding to identify additional suitable nucleic acid sources. The cells may be derived from human, murine, or other mammalian sources, including but not limited to rat, bovine, porcine, or various primate cells. Further, the T-cells may be stimulated with mitogens other than ConA or otherwise activated by conventional techniques. It is to be noted that human CD30/Fc was successfully employed to screen both human and murine cell lines in the foregoing assay (i.e., human CD30/Fc binds to a ligand on both the human and the murine cell lines tested).

EXAMPLE 3

Preparation of cDNA Library Derived from Activated Murine Helper T-cells

This example describes preparation of a cDNA library for expression cloning of murine CD30-L. The library was prepared from the murine helper T-cell line designated 7B9 (described above and in Mosley et al., *Cell* 59:335, 1989), which was stimulated for 6 hours with 3 $\mu$g/ml Con A. The library construction technique was substantially similar to that described by Ausubel et al., eds., *Current Protocols In Molecular Biology*, Vol. 1, (1987). Briefly, total RNA was extracted from the 7B9 cell line and poly $(A)^+$ mRNA was isolated by oligo dT cellulose chromatography. Double-stranded cDNA was made substantially as described by Gubier et al., *Gene* 25:263, 1983. Poly$(A)^+$ mRNA fragments were converted to RNA-cDNA hybrids by reverse transcriptase using random hexanucleotides as primers. The RNA-cDNA hybrids were then converted into double-stranded cDNA fragments using RNAase H in combination with DNA polymerase I. The resulting double-stranded cDNA was blunt-ended with T4 DNA polymerase.

Unkinased (i.e. unphosphorylated) BglII adaptors:

| | |
|---|---|
| 5'-GATCTGGCAACGAAGGTACCATGG-3' | (SEQ ID NO:11) |
| ACCGTTGCTTCCATGGTACC-5' | (SEQ ID NO:12) |

were ligated to 5' ends of the resulting blunt-ended cDNA, using the adaptor cloning method described in Haymerle et al., *Nucleic Acids Res.* 14:8615, 1986. Only the 24-mer oligonucleotide (top strand) will covalently bond to the cDNA during the ligation reaction. Non-covalently bound adaptors (including the 20-mer oligonucleotide above) were removed by gel filtration chromatography at 68° C. This left 24 nucleotide non-self-complementary overhangs on cDNA. The cDNA was inserted into pDC202, a mammalian expression vector that also replicates in *E. coli*. pDC202 is derived from pDC201 (Sims et al., *Nature* 241:585, 1988). The plasmid pCD201 was assembled from (i) the SV40 origin of replication, enhancer, and early and late promoters; (ii) the adenovirus-2 major late promoter and tripartite leader; (iii) SV40 polyadenylation and transcription termination signals; (iv) adenovirus-2 virus-associated RNA genes (VAI and VAII); and (v) pMSLV (Cosman et al., *Nature* 312:768, 1984). The multiple cloning site contains recognition sites for Kpn I, Sma I, and Bgl II. Certain extraneous vector sequences bordering the VA genes were excised from pDC201 to create pDC202. Each of the above-named features of pDC201 is present in pDC202 as well.

pDC202 was digested with BglII and Bgl II adaptors were ligated thereto as described for the cDNA above, except that the bottom strand of the adaptor (the 20-mer) is covalently bound to the vector, rather than the 24-mer ligated to the cDNA. A single-stranded extension complementary to that added to the cDNA thus was added to the BglII-digested vector. The 5' ends of the adaptored vector and cDNA were phosphorylated and the two DNA species were then ligated in the presence of T4 polynucleotide kinase. Dialyzed ligation mixtures were electroporated into *E. coli* strain DH5α and transformants selected on ampicillin plates.

To create an expression cloning library, the recombinant vectors containing 7B9-derived cDNA were transferred from *E. coli* to mammalian host cells. Plasmid DNA was isolated from pools of transformed *E. coli* and transfected into a sub-confluent layer of COS-7 cells using standard techniques. The transfected cells were cultured for two to three days on chambered glass slides (Lab-Tek) to permit transient expression of the inserted DNA sequences.

EXAMPLE 4

Isolation of Murine CD30-L cDNA

This example describes screening of the expression cloning library made in Example 3 with a labeled CD30/Fc fusion protein. The purified CD30/Fc fusion protein prepared in Example 1 was radioiodinated with $^{125}I$ using a commercially available solid phase agent (IODO-GEN, Pierce). In this procedure, 5 $\mu$g of IODO-GEN were plated at the bottom of a 10×75 mm glass tube and incubated for twenty minutes at 4° C. with 75 μl of 0.1 M sodium phosphate, pH 7.4 and 20 μl (2 mCi) Na$^{125}$I. The solution was then transferred to a second glass tube containing 5 μg of CD30/Fc in 45 μl PBS and this reaction mixture was incubated for twenty minutes at 4° C. The reaction mixture was fractionated by gel filtration on a 2 ml bed volume of Sephadex® G-25 (Sigma), and then equilibrated in RPMI 1640 medium containing 2.5% (v/v) bovine serum albumin (BSA), 0.2% (v/v) sodium azide and 20 mM Hepes, pH 7.4 binding medium. The final pool of $^{125}$I CD30/Fc was diluted to a working stock solution of 1×10$^{-7}$ M in binding medium, which may be stored for up to one month at 4° C. without detectable loss of receptor binding activity.

Monolayers of transfected COS-7 cells made in Example 3 were assayed by slide autoradiography for expression of CD30-L using the radioiodinated CD30/Fc fusion protein. The slide autoradiographic technique was essentially as described by Gearing et al., *EMBO J.* 8:3667, 1989. Briefly, transfected COS-7 cells were washed once with binding medium (RPMI 1640 containing 25 mg/ml bovine serum albumin (BSA), 2 mg/ml sodium azide, 20 mM Hepes pH 7.2, and 50 mg/ml nonfat dry milk) and incubated for 2 hours at 4° C. in binding medium containing 1×10$^{-9}$ M $^{125}$I-CD30/Fc fusion protein. After incubation, cells in the chambered slides were washed three times with binding buffer, followed by two washes with PBS, (pH 7.3) to remove unbound radiolabeled fusion protein.

The cells were fixed by incubating in 10% gluteraldehyde in PBS (30 minutes at room temperature), washed twice in PBS and air-dried. The slides were dipped in Kodak GTNB-2 photographic emulsion (5× dilution in water) and exposed in the dark for two to four days at room temperature in a light-proof box. The slides were developed in Kodak D19 developer, rinsed in water and fixed in Agfa G433C fixer. The slides were individually examined under a microscope at 25–40× magnification. Positive slides showing cells expressing CD30-L were identified by the presence of autoradiographic silver grains against a light background.

Eight pools, each containing approximately 2000 individual clones, were identified as positive for binding the CD30/Fc fusion protein. Two pools were titred and plated to provide plates containing approximately 200 colonies each. A replica of each breakdown pool was made and the cells were scraped to provide pooled plasmid DNA for transfection into COS-7 cells. The smaller pools were screened by slide autoradiography as described previously. Several of the breakdown pools contained clones that were positive for CD30-L as indicated by the presence of an expressed gene product capable of binding to the CD30/Fc fusion protein.

Individual colonies from two of the breakdown pools were picked from the replicas and inoculated into culture medium in individual wells of 96-well plates. Cultures were mixed by pooling rows and columns and the mixed cultures were used to prepare DNA for a final round of transfection and screening. An intersection of a positive row and a positive column identified the positive colony. DNA from the pure clone was isolated, retransfected and rescreened.

The recombinant plasmid containing murine CD30-L cDNA was recovered from the pure clone (COS-7 host cells) and transformed into *E. coli* strain DH5α. The mammalian expression vector pDC202 containing murine CD30-L cDNA (designated pDC202-mCD30-L) was deposited in *E. coli* strain DH5α host cells with the American Type Culture Collection, Rockville, Md. (ATCC) on May 28, 1992, under accession number ATCC 69004. The deposit was made under the terms of the Budapest Treaty.

A DNA sequence for the coding region of the cDNA insert of clone pDC202-mCD30-L is presented in SEQ ID NO:18, and, the encoded amino acid sequence is presented in SEQ ID NO:19. The protein comprises an N-terminal cytoplasmic domain (amino acids 1–27), a transmembrane region (amino acids 28–48), and an extracellular, i.e., receptor-binding domain (amino acids 49–220). This protein lacks a signal peptide.

Six amino acid triplets constituting N-linked glycosylation sites are found at amino acids 56–58, 67–69, 95–97, 139–141, 175–177, and 187–189 of SEQ ID NO:19. The protein comprises no KEX2 protease processing sites.

In this particular vector construction, an ATG codon located in the Bgl II adaptors (see Example 3) is in the same reading frame as the CD30-L cDNA insert. Thus, a percentage of the transcripts may comprise the following DNA sequence upstream of the sequence of SEQ ID NO:18. The encoded amino acids are also shown, and would be fused to the N-terminus of the SEQ ID NO:19 sequence, but are not CD30-L-specific amino acids.

```
ATG GGC TGT GGG GCT CCT TCC CCT GAC CCA GCC   (SEQ ID NO:13)

Met Gly Cys Gly Ala Pro Ser Pro Asp Pro Ala   (SEQ ID NO:14)
```

EXAMPLE 5

Monoclonal Antibodies Directed Against CD30-L

This example illustrates the preparation of monoclonal antibodies to CD30-L. CD30-L is expressed in mammalian host cells such as COS-7 or CV1-EBNA cells and purified using CD30/Fc affinity chromatography as described herein. Purified CD30-L can be used to generate monoclonal antibodies against CD30-L using conventional techniques, for example, those techniques described in U.S. Pat. No. 4,411,993. The immunogen may comprise a protein (or fragment thereof, such as the extracellular domain) fused to the peptide Asp-Tyr-Lys-Asp-Asp-Asp-Asp-Lys (DYKDDDDK) (SEQ ID NO:15) (Hopp et al., *Bio/Technology* 6:1204, 1988 and U.S. Pat. No. 5,011,912) or fused to the Fc portion of an antibody, as described above.

Briefly, mice are immunized with CD30-L as an immunogen emulsified in complete Freund's adjuvant, and injected in amounts ranging from 10–100 μg subcutaneously or intraperitoneally. Ten to twelve days later, the immunized animals are boosted with additional CD30-L emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked Immunosorbent Assay), for CD30-L antibodies.

Following detection of an appropriate antibody titer, positive animals are provided one last intravenous injection of CD30-L in saline. Three to four days later, the animals are sacrificed, spleen cells harvested, and spleen cells are fused to a murine myeloma cell line (e.g., NS1 or Ag 8.653). The latter myeloma cell line is available from the American Type Culture Collection as P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified CD30-L by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c mice to produce ascites containing high concentrations of anti-CD30-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to CD30-L.

EXAMPLE 6

Isolation of Human CD30-L cDNA

This example illustrates a cross-species hybridization technique which was used to isolate a human CD30-L cDNA using a probe derived from the sequence of murine CD30-L. A murine CD30-L probe was produced by excising the entire cDNA insert from murine clone pDC202-mCD30-L (ATCC 69004, described in Example 4) by Bgl II digestion, and $^{32}P$-labeling the fragment using random primers (Boehringer-Mannheim).

A human peripheral blood lymphocyte (PBL) cDNA library was constructed in a phage vector (λgt10). The PBL cells were obtained from normal human volunteers and treated with 10 ng/ml of OKT3 (an anti-CD3 antibody), and 10 ng/ml of human IL-2 (Immunex, Seattle, Wash.) for six days. The PBL cells were washed and stimulated with 500 ng/ml ionomycin (Calbiochem) and 10 ng/ml PMA (Sigma) for four hours. Messenger RNA was isolated from the stimulated PBL cells. cDNA synthesized on the mRNA template was packaged into λgt10 phage vectors (Gigapak®, Stratagene, San Diego, Calif.) according to manufacturer's instructions. Recombinant phage were then plated on *E. coli* strain KW251 and screened using standard plaque hybridization techniques.

The murine probe was hybridized to phage cDNA in the following hybridization buffer at 37° C. overnight:

50% Formamide 20 mM Pipes (pH 6.4)

0.8 M NaCl 2 mM EDTA 0.5% SDS 0.1 mg/ml salmon sperm DNA

Hybridization was followed by washing with 2×SSC, 0.1% SDS at 50° C. Positive (hybridizing) plaques were visualized by autoradiography.

Six of the positive plaques were purified and the inserts were isolated by PCR amplification using oligonucleotides that flank the cloning site. A partial amino acid sequence for human CD30-L was derived by determining the nucleotide sequence of a portion of one of these inserts (clone #9, about 2.0 kb in length). This partial amino acid sequence is presented in SEQ ID NO:20. The transmembrane region comprises amino acids 27–48 of SEQ ID NO:20. The amino acid represented by Xaa at position 6 is most likely a methionine residue encoded by an initiation codon. This partial human sequence exhibits significant homology to an N-terminal fragment of murine CD30-L, a preliminary amino acid sequence for which is presented as SEQ ID NO:21.

The DNA sequence of the entire coding region of the human CD30-L clone was determined and is presented in SEQ ID NO:22 and the encoded amino acid sequence is shown in SEQ ID NO:23. The N-terminal cytoplasmic domain (amino acids 1 to 21) is followed by a transmembrane region (amino acids 22 to 43) which is followed by the extracellular, i.e., receptor-binding domain (amino acids 44–215). This protein lacks a signal peptide. Where the partial human CD30-L of SEQ ID NO:20 differs from the full length human CD30-L amino acid sequence presented in SEQ ID NO:23, the SEQ ID NO:23 sequence is considered to be accurate. Comparison of the murine SEQ ID NO:19 and human (SEQ ID NO:23) CD30-L amino acid sequences using the above-described GAP computer program reveals 73% identity and 83% similarity between the two sequences.

Amino acid triplets that constitute potential N-linked glycosylation sites are found at positions 62–64, 90–92, 134–136, 170–172, and 182–184 in SEQ ID NO:23. A KEX2 protease processing site is found at amino acids 72–73. If desired, these N-glycosylation processing sites may be inactivated to preclude glycosylation as described above. The KEX2 sites may be inactivated to reduce proteolysis when the CD30-L protein is expressed in yeast cells, as described above.

The products of the above-described PCR reaction (by which the cDNA insert of the positive clone was amplified) were digested with EcoRI and ligated into an EcoRI-digested vector designated pGEMBL. Plasmid pGEMBL is a derivative of the standard cloning vector pBR322 and contains a polylinker having a unique EcoRI site along with several other unique restriction sites. The plasmid also comprises an ampicillin resistance gene. An exemplary vector of this type is described by Dente et al., (*Nucl. Acids Res.* 11:1645, 1983).

*E. coli* strain DH5α was transformed with the ligation mixture and transformants containing the desired recombinant plasmid were identified. Samples of *E. coli* DH5α containing plasmid hCD30-L/pGEMBL were deposited with the American Type Culture Collection, Rockville, Md. (ATCC) on Jun. 24, 1992, under accession number ATCC 69020. The deposit was made under the terms of the Budapest Treaty. The deposited recombinant plasmid contains human CD30-L DNA that includes the complete coding region shown in SEQ ID NO:22.

EXAMPLE 7

Isolation of Murine and Human CD30-L DNA Encoding Additional N-Terminal Amino Acids Because the CD30-L clones isolated in examples 4 and 6 had relatively short 5' noncoding regions and lacked stop codons upstream of the first initiation codon, isolation of CD30-L DNA comprising additional 5' sequences was attempted. An anchored PCR technique was employed, generally as described by Loh et al., *Science* 243:217 (1989) and Carrier et al., *Gene* 116:173 (1992), both of which are hereby incorporated by reference. The same procedures were employed for isolating murine and human clones, except as noted.

First strand cDNA was synthesized using a Superscript® cDNA kit (GIBCO/BRL, Gaithersburg, Md.) on the following mRNA templates:

murine: 5 μg total RNA from 7B9 cell line described in Example 3.

human: 2 μg poly $A^+$ RNA from human peripheral blood T-cells (the stimulated PBLs described in Example 6)

The primers employed in the cDNA synthesis (referred to as primers #1 hereinafter) were:

| | |
|---|---|
| murine: 5' AGATGCTTTGACACTTG 3' | (SEQ ID NO:16) |
| human: 5' ATCACCAGATTCCCATC 3' | (SEQ ID NO:17). |

Murine primer #1 is complementary to nucleotides 265–281 of SEQ ID NO:18. Human primer #1 is complementary to nucleotides 325–341 of SEQ ID NO:22.

The reaction mixture was treated with RNAse H, then purified over a Sephadex G50 spin column (Sigma). After drying, the cDNA was resuspended in: 10 μl $H_2O$, 4 μl 5× terminal deoxynucleotidyl transferase (TdT) buffer (as specified by GIBCO/BRL, Gaithersburg, Md.), 4 μl 1 mM dATP, and 1 μl TdT (15 units/μl). This reaction mixture was incubated at 37° C. for 10 minutes to add a poly-A tail to the 3' end of the cDNA. The reaction was stopped by heating at 68° C. for 15 minutes, and the mixture was applied to a Sephadex G50 spin column. The eluate was diluted to 250 μl with 10 mM Tris (pH 7.5), 1 mM EDTA. A first PCR reaction mixture was prepared by combining the first strand cDNA (tailed with adenines) with three primers in a conventional PCR reaction mixture. The primers were a first anchoring primer, a second anchoring primer, and a primer #2 (antisense).

The following reaction conditions (temperature cycles) were employed for this first PCR, and each of the PCRs described below:

| | |
|---|---|
| 94° C. - 5 minutes | - 1X |
| 94° C. - 0.5 minutes \| | |
| 55° C. - 1.5 minutes \| | - 30X |
| 72° C. - 2.5 minutes \| | |
| 72° C. - 5 minutes | - 1X |

The first anchoring primer contains a poly T segment that will anneal to the poly A tail added to the cDNA. This primer also inserts a NotI restriction site into the amplified DNA. The second anchoring primer, which lacks the poly T segment but is otherwise identical to the first anchoring primer, anneals (in later cycles of the reaction) to the NotI site-containing sequence inserted into the amplified DNA via the first anchoring primer.

The murine primer #2 is complementary to nucleotides 206–222 of SEQ ID NO:18. The human primer #2 is complementary to nucleotides 108–124 of SEQ ID NO:22.

A second PCR reaction mixture contained the products of the first PCR reaction, the 2nd anchoring primer, and primer #2. A third PCR reaction mixture contained the products of the second PCR reaction, the 2nd anchoring primer, and primer #3. The murine primer #3 contains a segment complementary to nucleotides 49–66 of SEQ ID NO:18. Human primer #3 contains a segment complementary to nucleotides 80–94 of SEQ ID NO:22. Each primer #3 also contains a segment that introduces a SalI restriction site into the amplified DNA.

PCR reaction products (from PCR reaction no. 2 for human and no. 3 for murine) were separated by electrophoresis on a 1% NuSieve agarose gel (FMC Bioproducts, Rockland, Me.). A PCR band comprising DNA of about 300 bp was isolated for both murine and human. The CD30-L DNA was further amplified in another PCR reaction. The reaction mixture comprised:

| | |
|---|---|
| 5 μl | band from gel (melted at 68° C.) |
| 10 μl | 10x buffer |
| 2 μl | 2nd anchoring primer |
| 2 μl | primer #3 |
| 1 μl | Taq DNA polymerase |
| 0.8 μl | 25 mM dNTP's |
| 79.2 μl | $dH_2O$ |
| 100.0 μl | TOTAL |

The nucleotide sequence of the reaction products was determined. The reaction products may be sequenced directly or subcloned by digesting with NotI/SalI prior to sequencing. Sequencing revealed additional DNA at the 5' end, compared to the clones of examples 4 and 6, including DNA encoding an additional 19 N-terminal amino acids for both murine and human CD30-L. DNA and encoded amino acid sequences for the coding region of CD30-L DNA comprising this additional 5' coding sequence are shown in SEQ ID NO:5 and SEQ ID NO:6 (murine) and SEQ ID NO:7 and SEQ ID NO:8 (human). The additional N-terminal amino acids comprise no N-glycosylation or KEX2 protease processing sites.

The murine and human CD30-L DNAs isolated in this example were expressed in CV1-EBNA cells. The molecular weight of the expressed protein, analyzed by non-reducing SDS-PAGE, was about 26,519 daltons for murine and 26,017 daltons for human CD30-L.

Although the murine and human CD-30-L proteins encoded by the clones of examples 4 and 6, respectively, are truncated at the N-terminus, the encoded proteins are biologically active in that they bind to CD30. Thus, CD30-L proteins lacking from one to all of the first 19 N-terminal amino acids shown in SEQ ID NOS:6 or 8 are biologically active CD30-L proteins of the present invention. Deletion of the first 19 amino acids of SEQ ID NOS:6 and 8 yields an amino acid sequence identical to that presented in SEQ ID NOS:19 and 23, respectively.

EXAMPLE 8

Analysis of Biological Activities of CD30-L

Cells on which CD30 expression has been previously observed were screened for a response to the recombinant CD30 ligand. Response to monoclonal antibodies that bind CD30 was also analyzed. The human cell types screened included activated T cells, three Hodgkin's lymphoma lines resembling H-RS cells with primitive B or T cell-like phenotypes, and a non-Hodgkin's lymphoma line of the large cell anaplastic lymphoma (LCAL) type.

Peripheral blood T-lymphocyte (PBT) cells were isolated by centrifugation over Histopaque (Sigma Chemical Co., St. Louis, Mo.) and rosetting with 2-amino-ethylisothiouronium bromide (AET)-treated sheep erythrocytes as described (Armitage et al., *Int. Immunol.* 2:1039 (1990)). The purified PBT were then cultured for 5 days in the presence of immobilized CD3 antibody and a titration of fixed CV1/EBNA cells expressing full length (membrane-bound) recombinant human CD30 ligand. In contrast to control cells transfected with vector alone, cells expressing CD30-L induced proliferation of the stimulated T-cells in a dose-dependent manner, with a maximal response observed with $2.5\times10^4$ CV1/EBNA cells/well. This enhanced proliferation (and other activities described below) could be blocked by the inclusion of 10 μg/ml of soluble CD30/Fc. Proliferation of CD3-activated T cells was also seen in the presence of immobilized anti-CD30 monoclonal antibody M44, suggesting the bivalent antibody mimics ligand-induced receptor cross linking. The M44 monoclonal antibody is a mouse IgG1 generated with purified CD30-Fc as immunogen, as described further in example 12. No response to CD30-L was seen in the absence of CD3 co-stimulation.

The biological activity of CD30-L on human lymphoma cell lines known to express CD30 was investigated. The $CD30^+$ human lymphoma lines tested included HDLM-2, KM-H2, L-428, and Karpas 299 cells. Culture conditions for these four cell lines are published (Drexler et al., *Leuk. Res.* 10:487 (1986); Gruss et al., *Cancer Res.* 52:3353 (1992)).

The HD-derived cell line HDLM-2 was established from a malignant pleural effusion of a 74-year-old male with endstage IVB HD (Drexler et al., 1986, supra; Gruss et al., 1992, supra). HDLM-2 is phenotypically T-cell-like (Gruss et al., 1992, supra). KM-H2 and L-428 are B cell-like, HD-derived lymphoma lines. The human Karpas 299 cell line was established from blast cells in the peripheral blood of a 25-year-old white male with the diagnosis of a large cell anaplastic lymphoma (Ki-1 positive high-grade human lymphoma). The peripheral blast cells with pleomorphic nuclei resembled primitive histiocytes, which bear the surface markers CD4, CD5, HLA-DR and CD30. The Karpas 299 cell line possesses the same cytochemical, immunologic, and chromosomal profile with a 2;5 translocation as the original peripheral blood blast cells of the patient (Fischer et al., *Blood* 72:234 (1988)).

The addition of CV1/EBNA cells (10,000 cells/well) expressing recombinant human CD30-L to the HD-derived cell line HDLM-2 (50,000 cells/well) resulted in enhanced proliferation, whereas addition of control CV1/EBNA cells transfected with vector alone had minimal effect. The CD30-L-induced stimulation of HDLM-2 cell proliferation was time-dependent, with a maximal 3–4-fold enhancement observed at 72 hours. Similar results were obtained using immobilized M44 antibody, and the effect was dose-dependent. Cells cultured with an isotype-matched control monoclonal antibody showed no response. Maximal enhancement of proliferation, a five-fold increase over control cultures, was detected after stimulation with 10 μg/ml of M44 for 72 hours. Here again, the M44 CD30 monoclonal antibody has agonist characteristics and mimics properties of the ligand. In contrast to the above results, no effects of CD30-L on proliferation or viability of the KM-H2 or L-428 cells were detected, even though both lines were confirmed to be $CD30^+$ by flow cytometry with M44.

A clear and dramatically different response to CD30-L was seen with the $CD30^+$ non-Hodgkin lymphoma (LCAL) line Karpas 299. The addition of either CV1/EBNA cells expressing the CD30-L or M44 antibody to Karpas 299 cells ($5\times10^3$ cells/well) decreased the proliferation eight-fold. This effect was further analyzed with cytotoxic assays measuring $^{51}Cr$-release. Both CV1/EBNA cells expressing CD30-L and M44 antibody induced specific $^{51}Cr$ release from these cells in a time and dose-dependent manner. At 18 hours, the specific release in response to CD30-L or M44 was 29.4% and 30.8%, respectively. The addition of CV1/EBNA cells transfected with vector alone, or of an isotype-matched control antibody, had no effect. Thus, in contrast to the enhanced proliferative response of the Hodgkin's lymphoma-derived HDLM-2, the response of the Karpas 299 non-Hodgkin's lymphoma line to CD30-L is cell death.

EXAMPLE 9

Northern Analysis of Murine and Human CD30-L Transcripts

Various types of cells were analyzed by Northern blotting to detect CD30-L transcripts (mRNA).

Human Cells

Human PBT cells, induced with a calcium ionophore, uninduced tonsillar T cells and LPS-induced monocytes all expressed a single hybridizing transcript migrating between 18 and 28 S ribosomal RNA. IL-7-treated PBT cells, PMA treated tonsillar B cells, uninduced Jurkat or LPS activated THP-1 macrophage, and GM-CSF treated monocytes did not express CD30-L. IL-1β induced low levels of CD30-L in monocytes. In addition, placental tissue, the promyelocytic HL60 line and two Burkitt's lymphoma B cell lines (Daudi and Raji) were also negative for expression of CD30-L transcripts. The HD-derived cell lines HDLM-2, KM-H2, and L-428, described in example 8, did not express CD30-L mRNA constitutively, or after stimulation with TPA for 24 to 72 hours or with 100 ng/mL IL-2 and TNF-α for 48 hours. Thus human CD30-L expression was detected on specifically induced T cells and monocytes/macrophages.

Murine Cells

The results on human cells are mirrored in the murine system. LPS stimulated bone marrow-derived macrophage, Con A activated 7F9 T cells (similar to the 7B9 murine helper T-cell line described in examples 2 and 3) and an LPS stimulated subclone of the murine thymoma EL4 (EL4 6.1) all express a single CD30-L transcript. Unstimulated EL4 6.1 and 7F9 cells, a bone marrow-derived stromal line D11 and a thymic stromal line F4, do not express CD30-L.

EXAMPLE 10

Characterization of Recombinant CD30-L

Biochemical characteristics of the recombinant, full-length cell surface forms of murine and human CD30-L were assessed by surface radioiodinating cells transiently expressing the recombinant ligands, then immunoprecipitating the ligands with CD30/Fc (and protein G) from lysates of detergent solubilized cells. Iodoacetamide (20 mM) was included in lysing and immunoprecipitation buffers to inhibit potential disulfide interchange. Washed precipitates were then displayed by SDS-PAGE with phosphorimaging. Cells transfected with vector only, or cells expressing recombinant ligand but immunoprecipitated with an isotype matched control (huIgG1), showed no bands. Under reducing conditions, the dominant product for both human and murine recombinant CD30-L is a diffuse 40 kd band. As the CD30-L protein molecular weight is 26,000 Kd, extensive use of the multiple N-linked glycosylation sites in the extracellular domains seems clear. Disulfide-linked dimers of human CD30-L appear under non-reducing conditions, and even higher oligomers, apparently disulfide-linked, are seen with murine CD30-L. Most, but not all of these are converted to monomers upon reduction. The fact that not all oligomers were converted to monomers may reflect either differential glycosylation and/or inefficient reduction.

EXAMPLE 11

Production of a Soluble Human CD30-L Fusion Protein

A soluble fusion protein comprising an antibody Fc region polypeptide joined through a peptide linker to the N-terminus of a fragment of the human CD30-L extracellular domain was produced and tested for biological activity as follows. DNA encoding a soluble human CD30-L polypeptide comprising amino acids 47 (Asp) to 215 (Asp) of SEQ ID NO:23 was isolated and amplified by PCR. The PCR was conducted by conventional procedures, using as the 5' primer an oligonucleotide comprising nucleotides 139–153 of SEQ ID NO:22 and a sequence containing a recognition site for BspE1. The 3' primer spanned the termination codon of CD30-L and contained the recognition sequence for Not I.

The PCR products were digested with Bsp E1 and Not I and the desired fragment was ligated into an expression vector designated pDC408, which is a derivative of the pDC406 vector described above. pDC408 had been modified to contain DNA encoding (in order) 5'-murine IL-7 leader sequence—FLAG®—human IgG1 Fc domain-peptide linker.

The murine IL-7 leader sequence is described in U.S. Pat. No. 4,965,195 and the FLAG® octapeptide is described above. The Fc polypeptide is described in example 1. A peptide linker of the sequence $Gly_4SerGly_5Ser$ was employed, and the soluble CD30-L encoding DNA was inserted immediately downstream of the peptide linker, in the same reading frame. 293 cells (ATCC CRL 1573; a transformed primary human embryonal kidney cell line) were transfected with the recombinant expression vector and cultured to permit expression and secretion of the fusion protein. The expressed protein was purified on a protein A column.

The activity of the expressed protein was measured using an inhibition assay in which the binding of $^{125}$I-labeled CD30/Fc protein to CD30-L expressed on the surface of transformed CV1/EBNA cells was measured. The soluble CD30-L-containing fusion protein was shown to be capable of inhibiting this binding, thus indicating its ability to bind to CD30/Fc. The measured affinity of the soluble ligand for CD30/Fc was roughly equivalent to that of CD30/Fc for the cell-bound ligand.

Alternatively, an expression vector is constructed that encodes a murine IL-7 leader sequence—FLAG®—soluble CD30-L fusion protein. The Fc polypeptide and peptide linker-encoding DNAs are omitted from this vector. Omitting the Fc polypeptide is advantageous in that aggregate formation is reduced. Dimers of CD30-L proteins without Fc moieties have been detected, as described in example 10. Including an Fc polypeptide may promote formation of undesirable aggregates of oligomers of CD30-L/Fc proteins.

EXAMPLE 12

Antibodies That Bind CD30

To generate monoclonal antibodies against the human CD30 antigen, CB6F1 mice (purchased from Jackson Laboratories, Bar Harbor, Me.) were boosted twice intradermally with 10 μg CD30/Fc in Ribi adjuvant (Ribi Immunochem Research, Hamilton, Mont.). The soluble human CD30/Fc fusion protein employed as the immunogen was produced as described in example 1. One week after the second boost, peroxidase dot blot assays using CD30/Fc showed a significant (>1/100) titer of anti-CD30 antibody in the serum. One week later, animals were boosted intravenously (IV) with 3 μg CD30/Fc into the tail vein. Three days later, spleen was removed and spleen cells were fused to the X63-Ag8.653 mouse myeloma cell line (Kearney et al., *J. Immunol.* 123:1548, 1979) by standard methods using a 50% polyethylene glycol/dimethyl sulfoxide solution (Sigma). Hybridoma cultures were established in 96-well plates (Costar, Cambridge, Mass.). Ten days later, culture supernatants were screened by an antigen capture assay using $^{125}$I-CD30/Fc. Ninety-six-well plates were coated overnight with goat-antimouse serum (Zymed, San Francisco, Calif.) and blocked with 3% bovine serum albumin (BSA; Sigma); 50 μL of culture supernatant was incubated for 1 hour at room temperature. After three washes with phosphate-buffered saline (PBS), plates were incubated with $^{125}$I-CD30/Fc for 1 hour and then washed with PBS again before being placed on film for overnight exposure. Positive wells were checked for reactivity with huIgG by performing an anti-brotin complex assay. Hybridoma cell lines reactive with HuIgG:horseradish peroxidase-CD30 were cloned. Positive supernatants were also tested by flow cytometry using CD30-expressing cells or CD30-transfected CV-1/EBNA cells.

Two human anti-CD30 monoclonal antibodies designated M44 and M67 (mouse $IgG_1$ isotype) were purified from spent bulk culture supernatants from two hybridoma cell lines produced above and grown in roller bottles. Antibodies were purified on a protein A affinity matrix using an automated purification system (BioRad MAPS system, Hercules, Calif.). Antibody concentration was determined by absorbance at 280 nm and purity assessed by sodium dodecyl sulfate (SDS) polyacrylamide gel electrophoresis and silver staining. Antibody concentrations were adjusted to 1 mg/mL and alliquots of purified antibody were stored frozen at −20° C. in 0.05 mol/L citrate buffer (pH 7.0).

EXAMPLE 13

Analysis of Biological Activities of CD30-L

Further studies of the response of cells expressing CD30 to the recombinant CD30 ligand were conducted. Response to monoclonal antibodies reactive with CD30 was also analyzed. These studies are similar to those described in example 8, but include additional cell lines and antibodies. The human cell types screened included activated T cells, four Hodgkin's lymphoma lines resembling H-RS cells with primitive B or T cell-like phenotypes, non-Hodgkin's lymphoma lines of the large cell anaplastic lymphoma (LCAL) type, and a T-cell leukemia (T-ALL) line.

Activated T-Cells.

Peripheral blood T-lymphocyte (PBT) cells were isolated from normal healthy human donors by centrifugation over Histopaque (Sigma Chemical Co., St. Louis, Mo.) and rosetting with 2-aminoethylisothiouronium bromide (AET)-treated sheep erythrocytes as described (Armitage et al., *Int. Immunol.* 2:1039 (1990)). Contaminating monocytes were removed by plastic adherence for 1 hour at 37° C. The resulting T-cell preparations were greater than 98% $CD3^+$, as determined by flow cytometric analysis. For activation of T-cells to induce CD30 expression, 96-well plates were coated with 10 μg/mL OKT3 (an anti-CD3-antibody; ATCC-CRL8001) in 50 mmol/L Tris buffer (pH 8.5) and washed twice with PBS. The purified T-cells ($1\times10^5$ cells/well) were then cultured for 72 hours in the presence of the immobilized anti-CD3 antibody and one of the following: a titration of fixed CV1/EBNA cells expressing full length (membrane-bound) recombinant human CD30 ligand; a titration of CV1/EBNA cells transformed with the empty expression vector alone; medium alone; a titration of immobilized anti-CD30 monoclonal antibody M44 or M67 (described in example 12); or a titration of an immobilized isotype-matched control antibody. The CV1/EBNA cells employed in the assay were transfected using the diethyl aminoethyl (DEAE)/Dextran method with either vector alone or a CD30L cDNA containing expression vector (CV-1/CD30L), and then fixed at 2 days posttransfection with 1% paraformaldehyde for 5 minutes at 25° C. The transformed CV1/EBNA cells were employed in the assay at $5\times10^4$ cells/well; the antibodies at a concentration of 10 $\mu$g/ml.

Cultures were pulsed with 1 $\mu$Ci/well $^3$H-thymidine ($^3$H.TdR; 25 Ci/mmol: Amersham, Arlington Heights, Ill.) for the final 12 hours of culture. Cells were harvested and incorporated cpm determined by tritum-sensitive avalanche gas ionization detection on a Matrix 96 Beta Counter (Packard, Meriden, Conn.).

Cells expressing murine or human CD30-L induced proliferation of the stimulated T-cells whereas no proliferative response was induced by medium or CV1/EBNA cells transformed with the empty vector. Proliferation of CD3-activated T-cells was also induced by the immobilized anti-CD30 monoclonal antibodies M44 and M67, suggesting the bivalent antibody mimics ligand-induced receptor cross linking. The activated T-cells did not respond to the irrelevant control antibody.

Lymphoma Cell Lines

The biological activity of CD30-L and anti-CD30 antibodies on human lymphoma cell lines known to express CD30 was investigated. The CD30$^+$ EBV$^-$ human lymphoma lines tested included the Hodgkins Disease (HD) derived lines HDLM-2, KM-H2, L-428, and L-540, and several LCAL-type non-Hodgkins' lymphoma lines. These cell lines and appropriate culture conditions are described in Drexler et al., *Leuk. Res.* 10:487 (1986); Gruss et al., *Cancer Res.* 52:3353 (1992); Kamesaki et al., *Blood* 68:285 (1986); Schaadt et al., *Int. J. Cancer* 26:723 (1980); and Diehl et al., *J. Cancer Res. Clin. Oncol.* 101:111 (1981).

The HD-derived cell line HDLM-2 was established from a malignant pleural effusion of a 74-year-old male with endstage IVB nodular sclerosis (NS) HD (Drexler et al., 1986, supra; Gruss et al., 1992, supra) and is phenotypically T-cell-like (Gruss et al., 1992, supra). KM-H2 and L-428 are B cell-like, HD-derived lymphoma lines. The L-428 cell line was derived from a malignant pleural effusion of a 37-year-old woman with endstage IVB NS HD; the KM-H2 cell line from a malignant pleural effusion of a 37-year-old man with stage IV mixed cellularity (MC) HD. The L-540 cell line, which is phenotypically T-cell-like, was derived from the bone marrow of a 20-year-old woman with stage IVB NS HD.

The human large cell anaplastic lymphoma cell line Karpas 299 was established from blast cells in the peripheral blood of a 25-year-old white male with the diagnosis of CD30$^+$ high-grade LCAL. The peripheral blast cells with pleomorphic nuclei resembled primitive histiocytes, which bear the surface markers CD4, CD5, epithelial membrane antigen (EMA), HLA-DR and CD30. The Karpas 299 cell line possesses the same cytochemical, immunologic, morphologic and chromosomal profile with a 2;5 translocation as the original peripheral blood blast cells of the patient (Fischer et al., *Blood* 72:234 (1988)). Seven additional permanent LCAL cell lines employed in the study were established from primary CD30$^+$ LCAL tumors, and resemble the malignant lymphoma clone of the primary LCAL patients.

Proliferative responses of the cell lines to CD30-L and anti-CD30 MAbs was analyzed in a thymidine incorporation assay similar to that described in example 8, as follows. A total of $5\times10^4$ HDLM-2, L-540, L-428, KM-H2 or LCAL (e.g., Karpas 299) cells were cultured for 72 hours with $1\times10^4$ CV-1/EBNA cells transfected with empty vector, with human or murine CD30-L encoding vectors, or with 10 $\mu$g/mL immobilized anti-CD30 MAbs M44, M67, and Ki-1 or isotype control MAb. The Ki-1 MAb (included in all but the assay on LCAL cells) was purchased from Dako Corporation, Santa Barbara, Calif. Tritiated-thymidine incorporation was determined after 72 hours.

No effects of CD30-L, M44, M67, or Ki-1 on proliferation or viability of the "B-cell-like" KM-H2 or L-428 cells were detected, even though both lines were confirmed to be CD30$^+$ by flow cytometry with anti-CD30 MAbs. In contrast, proliferation of the "T-cell-like" HD-derived cell lines HDLM-2 and L-540 was enhanced after addition of CD30-L or anti-CD30 MoAbs M44 and M67. Both murine and human CD30-L, expressed on CV-1 EBNA cells, induced a twofold to fivefold enhancement of $^3$H-thymidine uptake by HDLM-2 and L-540 H-RS cells compared with cells cultured with medium or CV-1/EBNA cells containing only the empty vector. Also, immobilized anti-CD30 MAbs M44 and M67 enhanced proliferation of HDLM-2 and L-540 cells threefold to eightfold. In contrast, the anti-CD30 MAb Ki-1 did not induce proliferation of HDLM-2 and L-540 cells above that induced by isotype-matched control antibody.

The CD30-L- and M44/M67-induced stimulation of HDLM-2 and L-540 cell proliferation was time- and dose-dependent. CD30-L induced maximal proliferation after 72 hours of culture. The MAbs M44 and M67 had maximal effects at concentrations of 10 $\mu$g/mL for a culture period of 48 to 72 hours. The enhanced proliferation effect of the CD30-L or the agonistic MAbs appeared to be specific because it could be blocked by the addition of 50-fold excess of soluble CD30/Fc protein. Here again, the M44 and M67 anti-CD30 monoclonal antibodies have agonist characteristics and mimic properties of the ligand.

A different response to CD30-L, M44 and M67 was seen with the CD30$^+$ non-Hodgkin lymphoma (LCAL) line Karpas 299. The addition of either CV1/EBNA cells expressing the CD30-L, or the M44 or M67 antibodies to Karpas 299 cells resulted in a threefold to sixfold reduction in proliferation in comparison to cells cultured with CV-1/EBNA cells transfected with the vector alone, isotype-matched control MAb, or medium. A significant reduction of $^3$H-thymidine uptake by Karpas 299 cells is measurable after 24 hours in culture with CD30-L, M44, or M67. The reduction of proliferation was time-dependent (being minimal 72 hours after initiation of the cultures), dose-dependent, and could be almost completely reversed by the addition of a 50-fold excess of soluble CD30/Fc. Only one of the seven additional LCAL cell lines did not show an alteration of proliferation after the addition of membrane-expressed CD30-L or anti-CD30 MAbs M44 and M67. A 30% to 70% reduction of proliferation in response to CD30-L, M44, and M67, in comparison to the controls, was seen for the other LCAL lines.

T-Cell Leukemia Cell Line

The proliferative response of an adult T-cell leukemia (T-ALL) cell line designated KE-37 to CD30-L (human only) and antibodies M44 and M67 was analyzed in the above-described thymidine incorporation assay. The recombinant CD30-L and both anti-CD30 antibodies induced enhanced proliferation of the KE-37 cells. No proliferative response was seen for any of the controls (including the antibody Ki-1).

What is claimed is:

1. A purified oligomer comprising CD30 ligand (CD30-L) polypeptides, wherein the CD30-L polypeptides are each selected from the group consisting of:

a) the murine CD30-L of SEQ ID NO:6;

b) the murine CD30-L of SEQ ID NO:19;

c) the human CD30-L of SEQ ID NO:8;

d) the human CD30-L of SEQ ID NO:23; and e) a fragment of the CD30-L of (a), (b), (c), or (d), wherein said fragment binds CD30.

2. An oligomer according to claim 1, wherein said oligomer comprises three CD30-L polypeptides.

3. An oligomer according to claim 1, wherein each of the CD30-L polypeptides is selected from the group consisting of:

a) a soluble CD30-L polypeptide comprising the extracellular domain of a CD30-L, encoded by a DNA sequence that will hybridize to the nucleotide sequence presented in SEQ ID NO:18 or SEQ ID NO:22 under moderately stringent conditions of 55° C. in 5×SSC, and b) a fragment of an extracellular domain of (a), wherein said extracellular domain and said fragment bind CD30.

4. An oligomer according to claim 1, wherein each of the CD30-L polypeptides is a soluble fragment of the human CD30-L of SEQ ID NO:8 or SEQ ID NO:23.

5. An oligomer according to claim 4, wherein said oligomer comprises three CD30-L polypeptides.

6. An oligomer according to claim 4, wherein each of the CD30-L polypeptides is selected from the group consisting of a polypeptide comprising the extracellular domain of the human CD30-L of SEQ ID NO:23, and a fragment of said extracellular domain, wherein said fragment binds CD30.

7. An oligomer according to claim 6, wherein said oligomer comprises three CD30-L polypeptides.

8. A purified CD30-L polypeptide, wherein said polypeptide is a fragment of a protein selected from the group consisting of:

a) the murine CD30-L protein of SEQ ID NO:6;

b) the murine CD30-L protein of SEQ ID NO:19;

c) the human CD30-L protein of SEQ ID NO:8; and d) the human CD30-L protein of SEQ ID NO:23;

wherein said fragment binds CD30.

* * * * *